US012226543B2

(12) United States Patent
Lake et al.

(10) Patent No.: US 12,226,543 B2
(45) Date of Patent: Feb. 18, 2025

(54) pH SENSITIVE COLOR INDICATOR FOR SANITIZING APPLICATIONS

(71) Applicant: ECOLAB USA INC., Saint Paul, MN (US)

(72) Inventors: Kaitlin Lake, Saint Paul, MN (US); Conor Smith, Saint Paul, MN (US); Karl Heinbuch, Saint Paul, MN (US); Matthew Paul Molinaro, Saint Paul, MN (US)

(73) Assignee: ECOLAB USA INC., Saint Paul, MN (US)

( * ) Notice: Subject to any disclaimer, the term of this patent is extended or adjusted under 35 U.S.C. 154(b) by 609 days.

(21) Appl. No.: 16/871,772

(22) Filed: May 11, 2020

(65) Prior Publication Data

US 2020/0353118 A1 Nov. 12, 2020

Related U.S. Application Data

(60) Provisional application No. 62/846,144, filed on May 10, 2019.

(51) Int. Cl.
*A61L 2/28* (2006.01)
*G01N 21/80* (2006.01)
*G01N 31/22* (2006.01)

(52) U.S. Cl.
CPC ............... *A61L 2/28* (2013.01); *G01N 21/80* (2013.01); *G01N 31/226* (2013.01)

(58) Field of Classification Search
None
See application file for complete search history.

(56) References Cited

U.S. PATENT DOCUMENTS

| 3,926,830 A | 12/1975 | Horiguchi et al. |
| 3,930,407 A | 1/1976 | Alburger |
| 4,029,598 A * | 6/1977 | Neisius ............... G01N 31/221 436/163 |
| 4,298,569 A | 11/1981 | Read |
| 4,311,479 A | 1/1982 | Fenn et al. |
| | (Continued) | |

FOREIGN PATENT DOCUMENTS

| AU | 2006236076 A1 | 12/2006 |
| BE | 773003 A | 3/1972 |
| | (Continued) | |

OTHER PUBLICATIONS

International Searching Authority in connection with PCT/US2020/032344 filed May 11, 2020, "Written Opinion of the International Preliminary Examining Authority", 7 pages, mailed Apr. 13, 2021.

(Continued)

*Primary Examiner* — Lore R Jarrett
(74) *Attorney, Agent, or Firm* — McKee, Voorhees & Sease, PLC

(57) ABSTRACT

The disclosure relates to pH sensitive color indicators which indicate the efficacy of a cleaning composition for antimicrobial activity by exhibiting a color change. In particular, the pH sensitive color indicators comprise a pH sensitive dye and a substrate, wherein the dye is bound to the substrate. In an aspect of the disclosure, the dye can be chemically bound, physically bound, coated on a substrate, or painted on a substrate.

20 Claims, 24 Drawing Sheets

(56) References Cited

U.S. PATENT DOCUMENTS

| | | | |
|---|---|---|---|
| 4,532,216 | A | 7/1985 | Wang |
| 4,678,704 | A | 7/1987 | Fellows |
| 4,800,066 | A | 1/1989 | Sinclair et al. |
| 4,855,239 | A | 8/1989 | Rupe |
| 5,242,602 | A | 9/1993 | Richardson et al. |
| 5,374,536 | A | 12/1994 | Robertson |
| 5,498,547 | A | 3/1996 | Blake et al. |
| 5,523,075 | A | 6/1996 | Fuerst et al. |
| 5,558,840 | A * | 9/1996 | Jones ................ A61B 10/007 215/396 |
| 5,565,363 | A | 10/1996 | Iwata et al. |
| 6,257,440 | B1 * | 7/2001 | Perkins ................ B65D 25/32 220/760 |
| 6,277,646 | B1 * | 8/2001 | Guirguis ................ B01L 3/502 422/417 |
| 6,329,207 | B1 | 12/2001 | Fricker et al. |
| 6,395,551 | B1 | 5/2002 | Kipke et al. |
| 6,410,338 | B1 | 6/2002 | Lippold et al. |
| 7,033,990 | B2 | 4/2006 | Dundale et al. |
| 7,112,448 | B2 | 9/2006 | Zhu et al. |
| 7,282,349 | B2 | 10/2007 | Lye et al. |
| 7,393,450 | B2 | 7/2008 | Silveri |
| 7,727,468 | B2 | 6/2010 | Herrlein et al. |
| 8,071,390 | B2 | 12/2011 | Tokhtuev et al. |
| 8,124,169 | B2 | 2/2012 | Ylitalo et al. |
| 8,343,908 | B2 | 1/2013 | Mundschau et al. |
| 8,440,606 | B2 | 5/2013 | Mundschau et al. |
| 8,481,331 | B2 | 7/2013 | Cregger et al. |
| 8,772,184 | B2 | 7/2014 | Farrugia et al. |
| 8,772,185 | B2 | 7/2014 | Jelonek et al. |
| 8,846,594 | B2 | 9/2014 | Seita et al. |
| 9,144,620 | B2 | 9/2015 | Balz et al. |
| 9,170,205 | B2 | 10/2015 | Burns et al. |
| 9,228,986 | B2 | 1/2016 | Xiao et al. |
| 9,599,566 | B2 | 3/2017 | Zheng |
| 9,625,392 | B2 | 4/2017 | Herzog et al. |
| 2002/0051733 | A1 | 5/2002 | Antonoplos et al. |
| 2003/0021727 | A1 * | 1/2003 | Weyker ................ A61B 10/007 436/169 |
| 2003/0220213 | A1 | 11/2003 | Bober |
| 2004/0038848 | A1 | 2/2004 | Kritzler |
| 2004/0184965 | A1 * | 9/2004 | Smith ................ B01L 3/508 422/400 |
| 2006/0293205 | A1 | 12/2006 | Chung |
| 2007/0276207 | A1 | 11/2007 | Fagland et al. |
| 2008/0223413 | A1 | 9/2008 | Radford |
| 2009/0057619 | A1 | 3/2009 | Goldman et al. |
| 2009/0093063 | A1 | 4/2009 | Anslyn et al. |
| 2009/0124526 | A1 | 5/2009 | De Leersnyder et al. |
| 2009/0185956 | A1 | 7/2009 | Junger et al. |
| 2010/0112680 | A1 | 5/2010 | Brockwell et al. |
| 2010/0270197 | A1 * | 10/2010 | Porret ................ C07F 9/5537 206/459.1 |
| 2011/0003391 | A1 * | 1/2011 | Boyette ................ C08J 5/18 422/423 |
| 2011/0024421 | A1 * | 2/2011 | Luburic ................ B65D 43/161 220/265 |
| 2011/0158917 | A1 | 6/2011 | MacDonald et al. |
| 2012/0093736 | A1 | 4/2012 | Jelonek et al. |
| 2012/0208733 | A1 | 8/2012 | Quarles |
| 2013/0168279 | A1 | 7/2013 | Sandford |
| 2013/0243645 | A1 | 9/2013 | Balz et al. |
| 2013/0323854 | A1 | 12/2013 | Kraus et al. |
| 2014/0242716 | A1 | 8/2014 | Hartselle |
| 2016/0258927 | A1 | 9/2016 | Sawa |
| 2016/0298063 | A1 | 10/2016 | Behr et al. |
| 2017/0071200 | A1 | 3/2017 | McSherry et al. |
| 2018/0003644 | A1 | 1/2018 | Christiansen |
| 2019/0011436 | A1 | 1/2019 | Dellimore et al. |

FOREIGN PATENT DOCUMENTS

| | | | |
|---|---|---|---|
| BE | 864775 | A | 9/1978 |
| CN | 201434787 | Y | 3/2010 |
| DE | 2147268 | A1 | 3/1972 |
| DE | 2403229 | A1 | 8/1974 |
| DE | 102009050798 | A1 | 4/2011 |
| EP | 1155109 | B1 | 4/2006 |
| FR | 2198991 | B1 | 8/1977 |
| FR | 2673640 | B1 | 8/1994 |
| GB | 2216655 | B | 10/1989 |
| IN | 200900670 | | 6/2009 |
| IN | 20117293 | | 10/2013 |
| IN | 201300182 | | 9/2014 |
| IN | 201302823 | | 6/2016 |
| JP | 5116048 | | 5/1976 |
| JP | 5273193 | A | 6/1977 |
| JP | 6034621 | A | 2/1985 |
| JP | 62261060 | A | 11/1987 |
| JP | H04291153 | A | 10/1992 |
| JP | 789114 | B2 | 9/1995 |
| JP | H0885550 | A | 4/1996 |
| JP | H10282002 | A | 10/1998 |
| JP | 2006308423 | A | 11/2006 |
| JP | 201229770 | A | 2/2012 |
| JP | 4901592 | B2 | 3/2012 |
| JP | 6023764 | B2 | 11/2016 |
| JP | 6073728 | B2 | 2/2017 |
| KR | 101605193 | B1 | 3/2016 |
| KR | 101923815 | B1 | 11/2018 |
| MX | 01008617 | A | 7/2002 |
| MX | 02006182 | A | 12/2002 |
| MX | 04008030 | A | 11/2004 |
| MX | 283834 | B | 10/2006 |
| MX | 2008005351 | A | 4/2008 |
| MX | 3347 | B | 3/2010 |
| MX | 2011013562 | A | 1/2012 |
| PL | 215147 | B1 | 10/2013 |
| WO | 0002845 | A1 | 1/2000 |
| WO | 0075237 | A3 | 12/2000 |
| WO | 0187132 | A1 | 11/2001 |
| WO | 0224846 | A2 | 3/2002 |
| WO | 0246743 | A2 | 6/2002 |
| WO | 0050554 | A1 | 8/2003 |
| WO | 2006091465 | A1 | 8/2006 |
| WO | 2007050463 | A1 | 5/2007 |
| WO | 2007054238 | A1 | 5/2007 |
| WO | WO2007141775 | A2 * | 12/2007 ............ A47L 13/58 |
| WO | 2008074635 | A1 | 6/2008 |
| WO | 2009005936 | A1 | 1/2009 |
| WO | 2014102556 | A1 | 7/2014 |
| WO | 2016090469 | A1 | 6/2016 |
| WO | 2016120165 | A1 | 8/2016 |
| WO | 2017205474 | A1 | 11/2017 |
| WO | 2018222410 | A1 | 12/2018 |
| WO | 2019014470 | A1 | 1/2019 |
| ZA | 20016052 | B | 9/2002 |

OTHER PUBLICATIONS

International Searching Authority, "International Search Report and Written Opinion of the International Searching Authority", based on PCT/US2020/032344, filed May 11, 2020, 16 pages, mailed Oct. 19, 2020.

First Office Action in CN202080034554.7, mailed Sep. 9, 2023, 41 pages.

"Textbook of Pharmaceutical Chemistry," Senov (USSR), Beijing People's Medical Publishing House, Aug. 1957, pp. 258-263.

Xin et al., "Progress of Optical Fiber pH Chemical Sensor," Laser & Optoelectronics Progress, Feb. 2011, 8 pages.

* cited by examiner pH SENSITIVE COLOR INDICATOR FOR SANITIZING APPLICATIONS

CROSS-REFERENCE TO RELATED APPLICATIONS

This application claims priority under 35 U.S.C. § 119 to provisional application Ser. No. 62/846,144, filed May 10, 2019, herein incorporated by reference in its entirety.

TECHNICAL FIELD

The disclosure relates to pH sensitive indicators for sanitizing applications. In particular, pH sensitive materials that indicate sufficient concentration of a sanitizing composition.

BACKGROUND

Use of various cleaning compositions, including in particular sanitizing compositions, it is important that the compositions be used at a sufficient concentration for effective sanitizing, disinfectant, and/or cleaning. Various mechanisms have been employed to assess the concentration of the compositions largely focusing on measuring the active species. For example, in chlorine-based or quaternary ammonium-based compositions, the amount of chlorine or quaternary ammonium compound is often measured to assess whether the composition has a sufficient concentration for the particular cleaning application, e.g., sufficient to sanitize or disinfect. The traditional mechanisms for measuring the concentration of the compositions suffer a number of drawbacks. For example, in some situations expensive test equipment is required to measure the concentrations. Another drawback includes the need to analyze, interpret, and apply results to determine whether the active species concentration indicates a sufficient concentration for the particular application. Still another drawback is that the tests may not be able to provide real-time results regarding the concentration at an end use application. Finally, due to changes in stability of some components or equilibrium of chemistry, it has been necessary for personnel to test and assess the concentration of critical components in each bucket, sink, pail, or spray bottle prior to use to ensure the concentration is sufficient for the degree of cleaning, e.g., sanitizing or disinfecting.

Accordingly, there is a need for improved methods and mechanisms of assessing the concentration of a cleaning composition.

It is an objective of the present disclosure to provide methods and mechanisms for assessing the concentration of a cleaning composition.

Still a further object of the present disclosure is to provide a method and mechanism that provides concentration information in real-time, at a glance, without the need for analysis and interpretation.

Other objects, advantages and features of the present invention will become apparent from the following specification taken in conjunction with the accompanying figures.

BRIEF SUMMARY

An advantage of the pH sensitive color indicators disclosed herein is that they provide a real-time indicator of the concentration of a cleaning composition. Another advantage of the pH sensitive color indicators is that they provide a simple mechanism for determining whether an acceptable concentration of a sanitizing or disinfecting composition exists with a mechanism permitting an at-a-glance determination.

At least one embodiment disclosed herein comprises a distinct aesthetic appearance. Ornamental aspects included in such an embodiment can help capture a consumer's attention and/or identify a source of origin of a product being sold. Said ornamental aspects will not impede functionality of the present invention.

A preferred embodiment, as described herein, comprises a pH sensitive indicator comprising an azo dye and a substrate; wherein the azo dye is bound to or coated on the substrate; wherein the azo dye exhibits a color change at a pH of about 4.5 or less. A further embodiment, as described herein, comprises a method of detecting a concentration of a cleaning composition comprising contacting a cleaning composition with a pH sensitive indicator; wherein the pH sensitive indicator comprises an azo dye and a substrate; wherein the azo dye is bound to or coated on the substrate; wherein the azo dye exhibits a color change at a pH of about 4.5 or less; wherein the substrate is a plastic, a metal, a textile, or cellulose based; determining whether the cleaning composition has a concentration efficacious for a cleaning application by observing whether the pH sensitive indicator exhibited a color change during or after the contacting step.

Another preferred embodiment, as described herein, comprises a method of cleaning a surface comprising contacting a cleaning composition with a pH sensitive indicator; wherein the pH sensitive indicator comprises an azo dye and a substrate; wherein the azo dye is bound to or coated on the substrate; wherein the azo dye exhibits a color change at a pH of about 4.5 or less; and wherein the substrate is a plastic, a metal, a textile, or cellulose based; determining whether the cleaning composition has a low enough pH by observing whether the pH sensitive indicator exhibited a color change during or after the contacting step; and applying the cleaning composition to a surface if a color change was exhibited.

While multiple embodiments are disclosed, still other embodiments will become apparent to those skilled in the art from the following detailed description, which shows and describes illustrative embodiments of the invention. Accordingly, the figures and detailed description are to be regarded as illustrative in nature and not restrictive.

Figure 1:
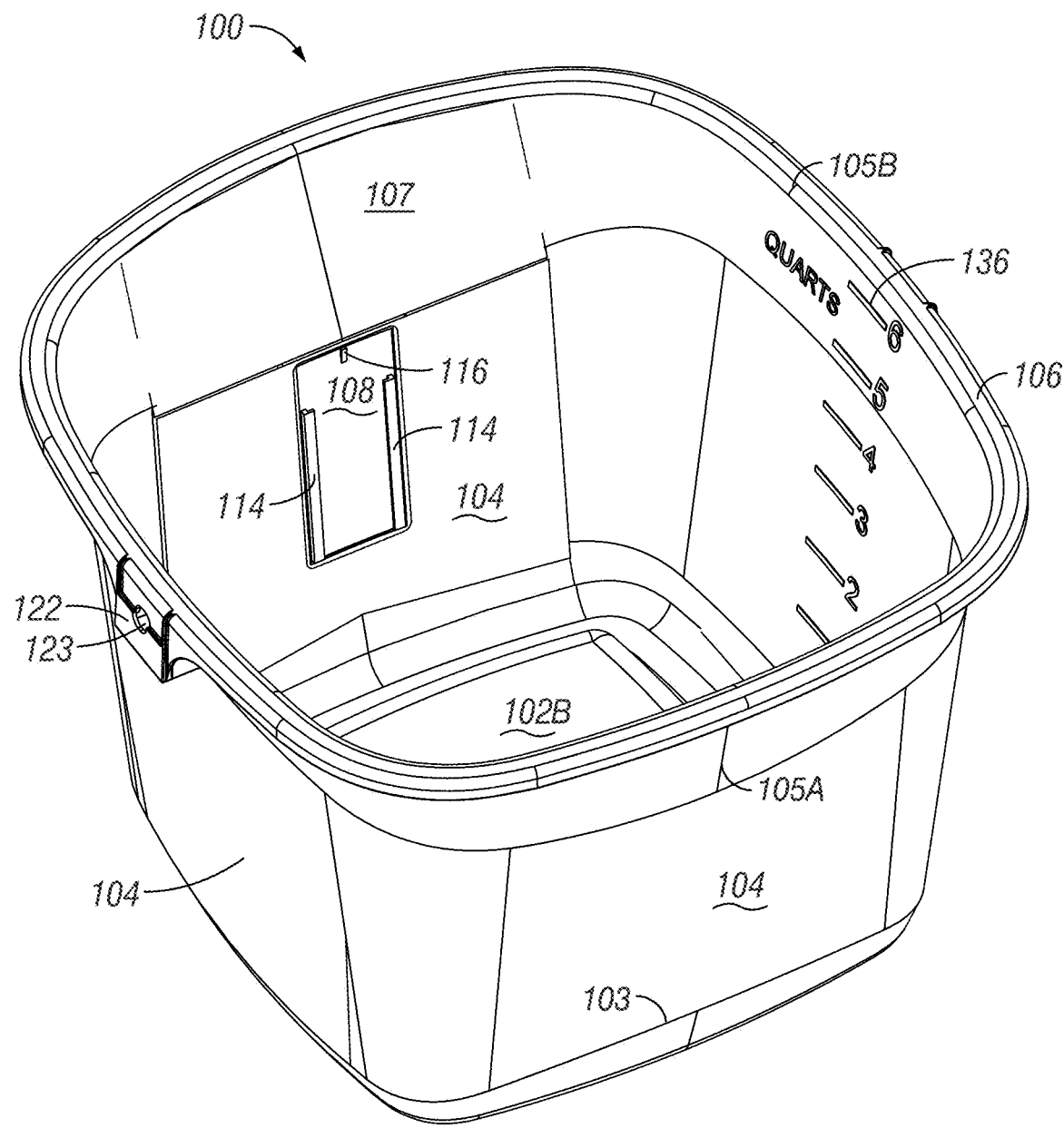
FIG. 1 shows a rear, top perspective view of a pail with substantially transparent windows.
Figure 2:
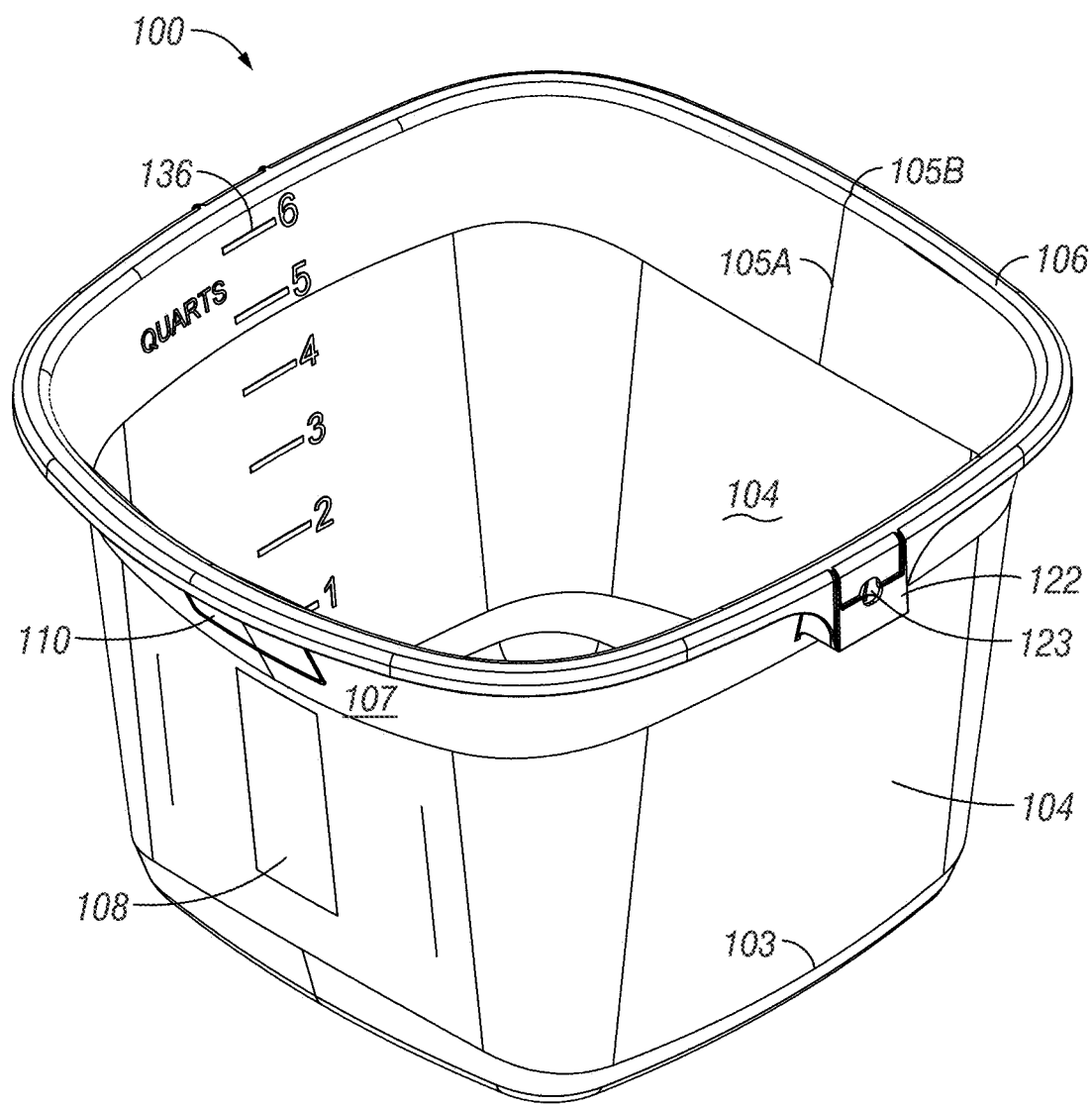
FIG. 2 shows a front, top perspective view thereof.
Figure 3:
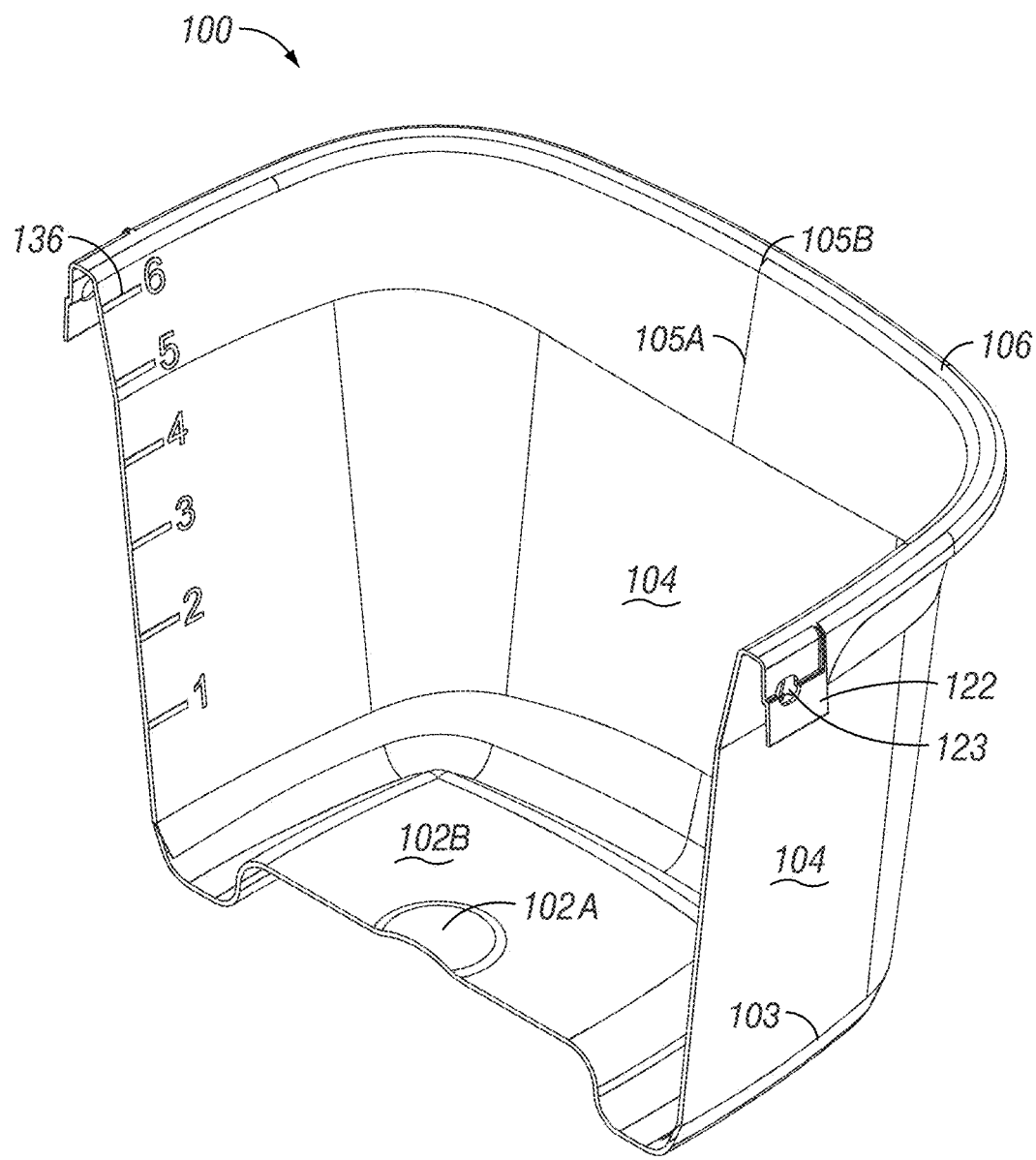
FIG. 3 shows an xz cross-sectional perspective view thereof.
Figure 4:
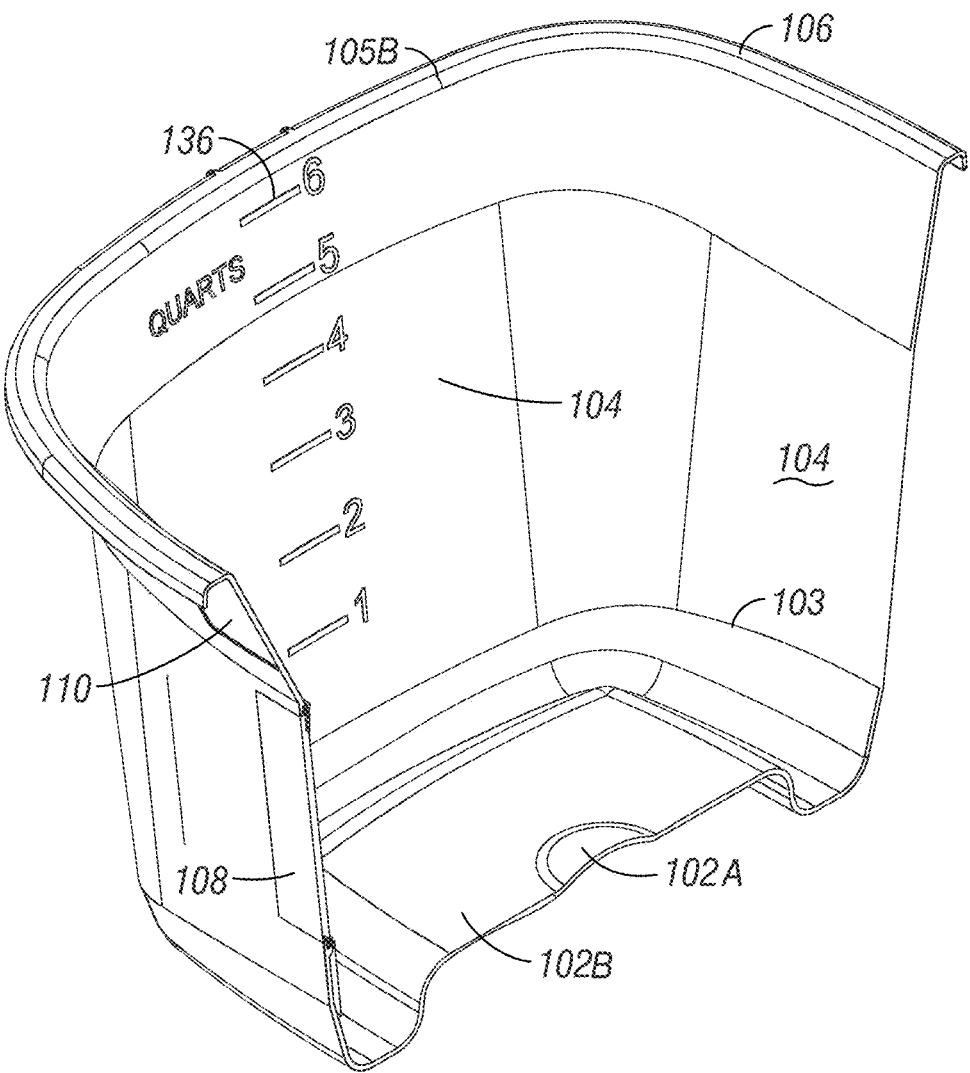
FIG. 4 shows an xy cross-section perspective view thereof.
Figure 5:
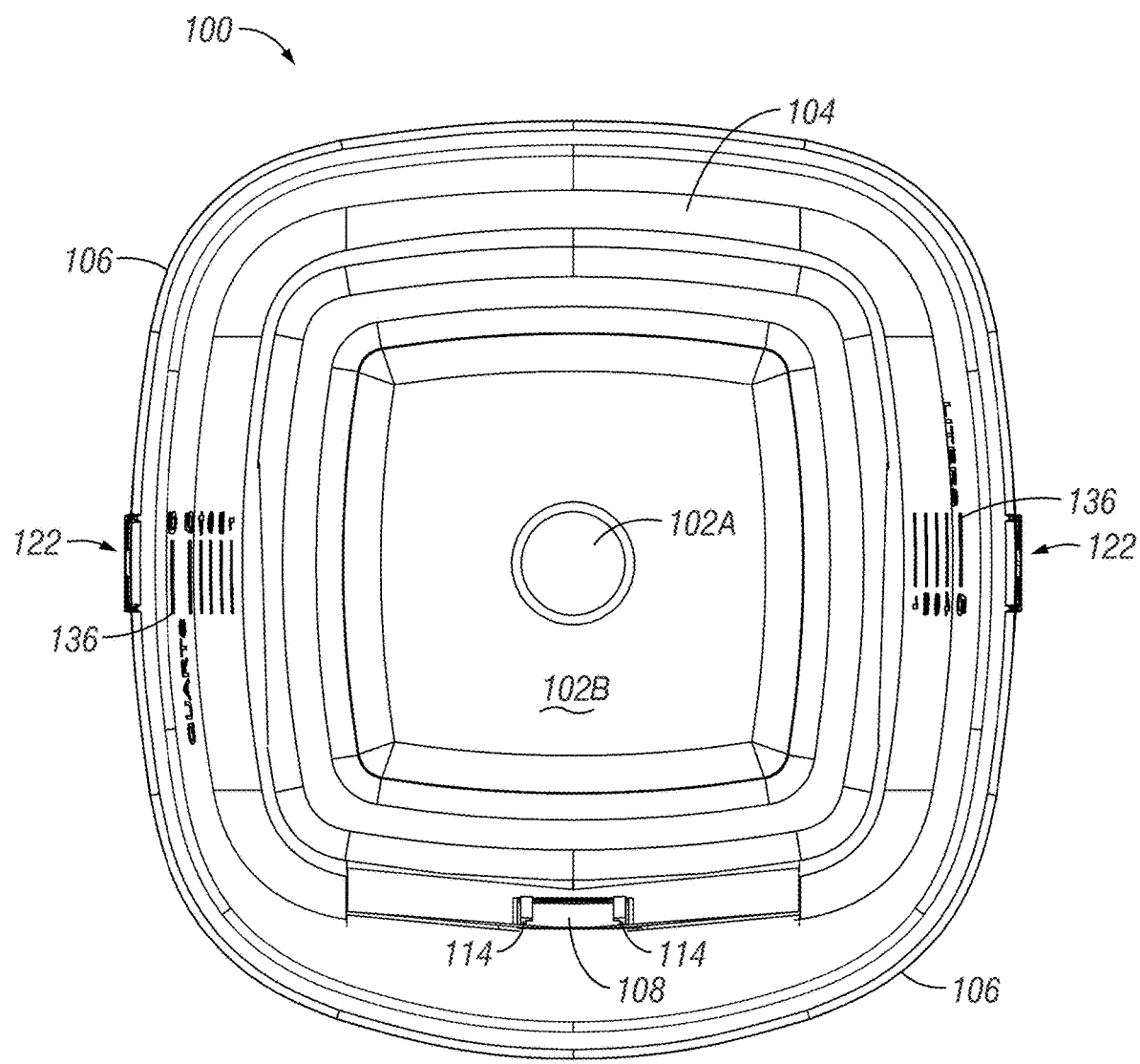
FIG. 5 shows a top elevational view thereof.
Figure 6:
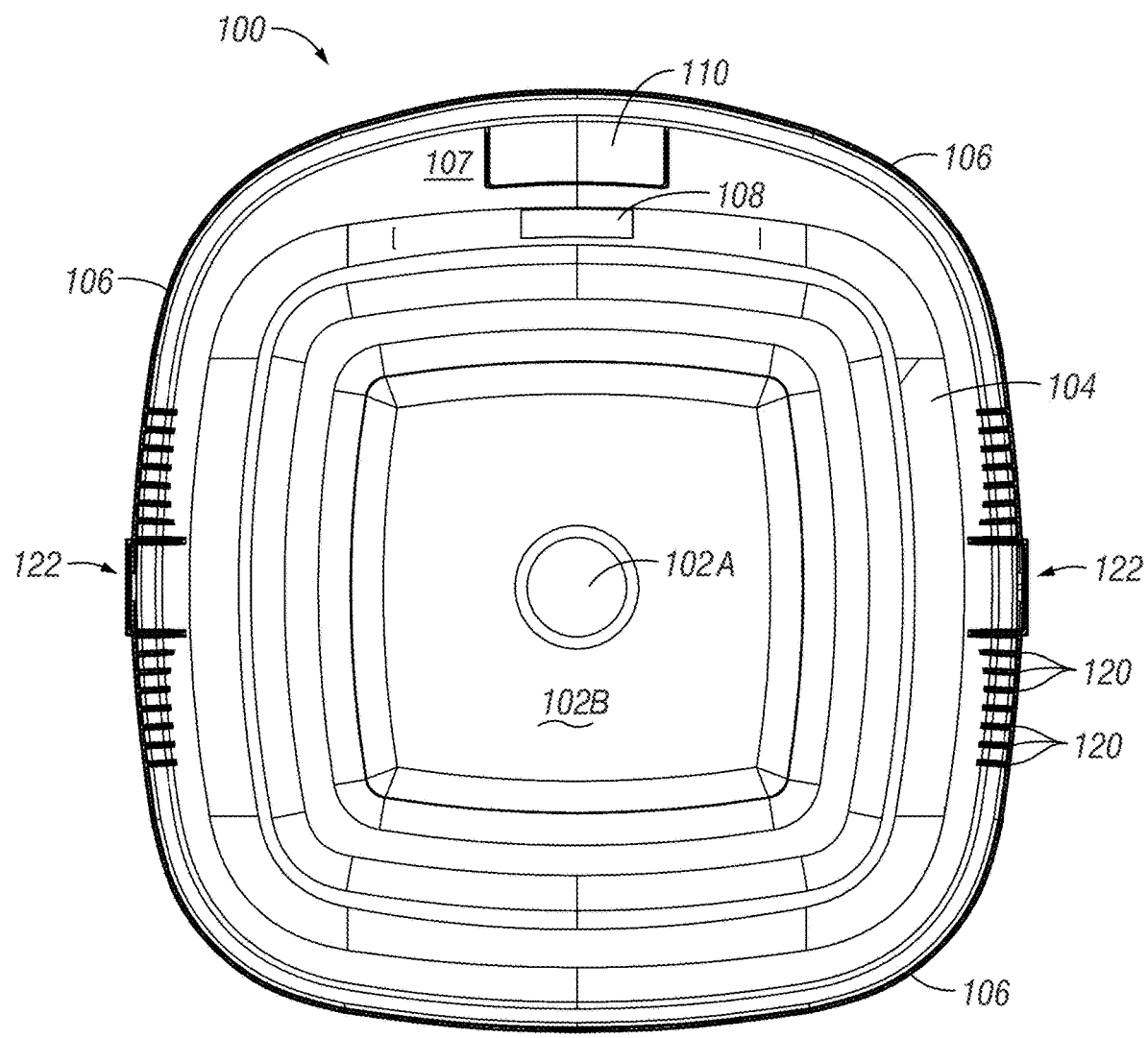
FIG. 6 shows a bottom elevational view thereof.
Figure 7:
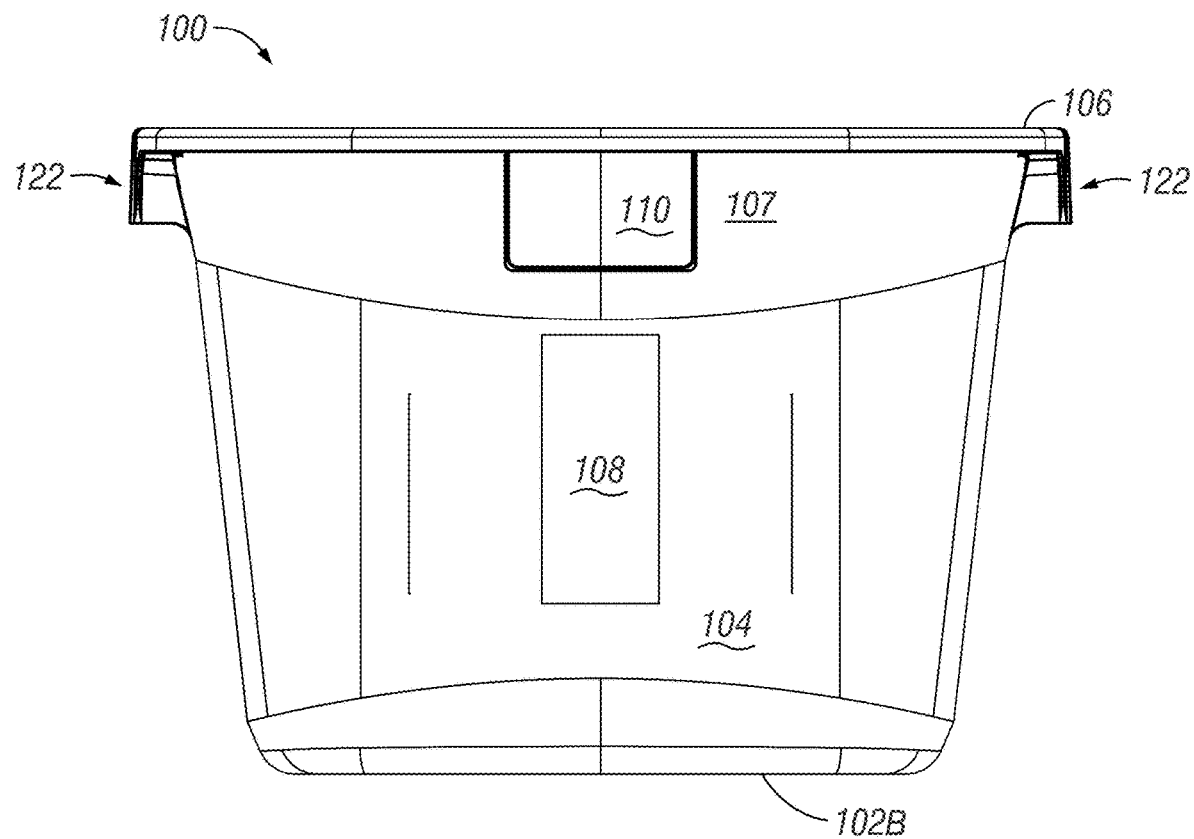
FIG. 7 shows a front elevational view thereof.
Figure 8:
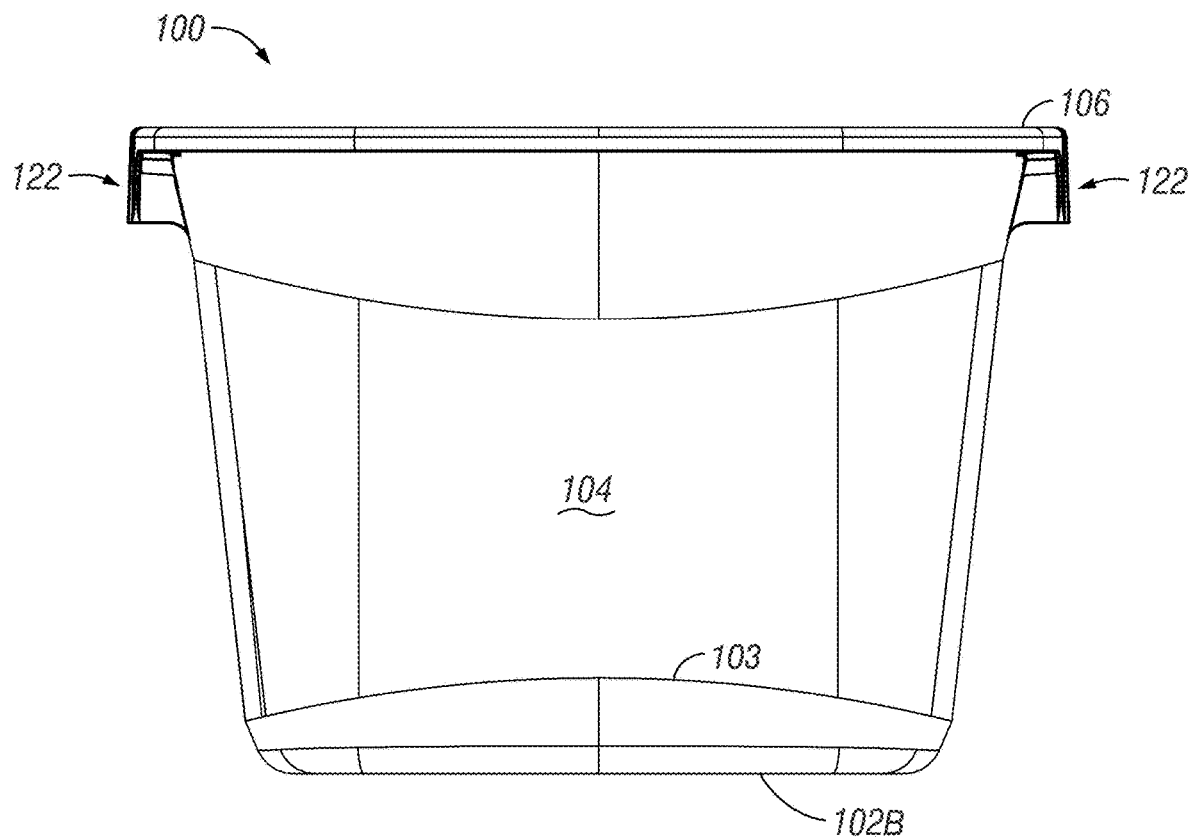
FIG. 8 shows a rear elevational view thereof.
Figure 9:
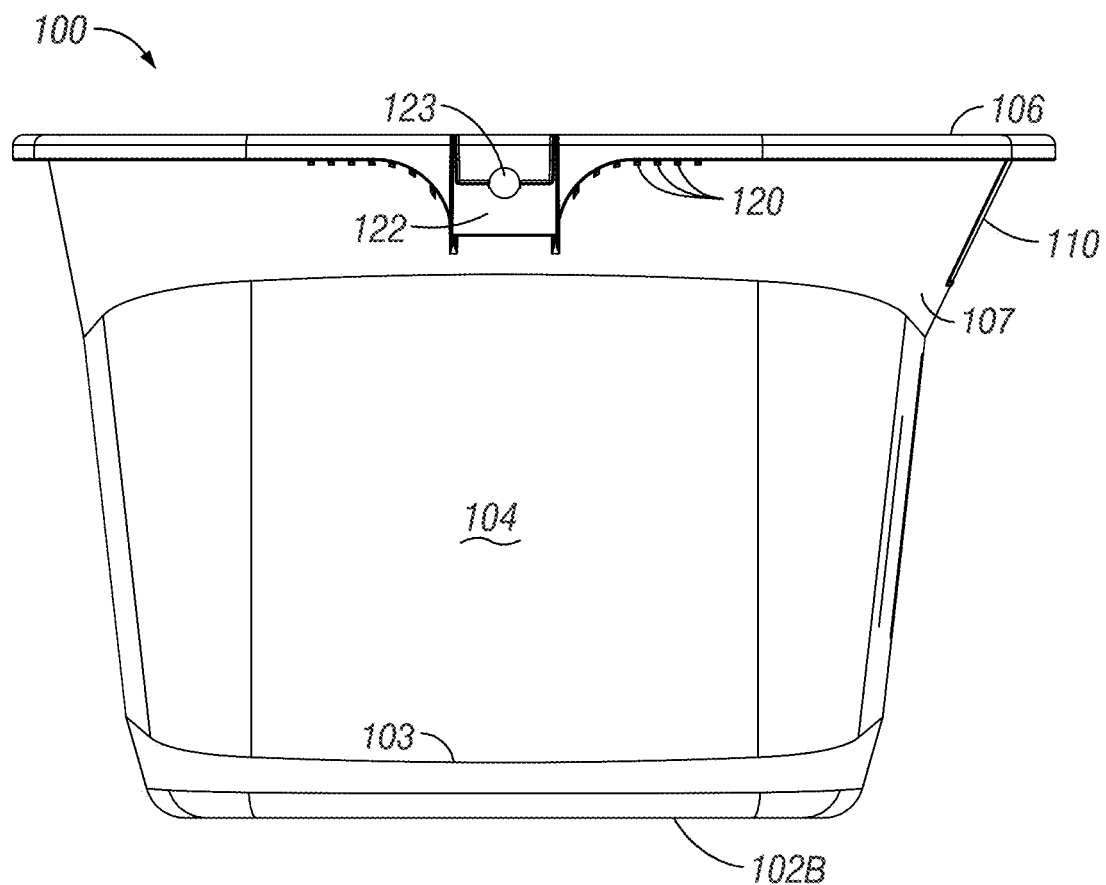
FIG. 9 shows a left-side elevational view thereof.
Figure 10:
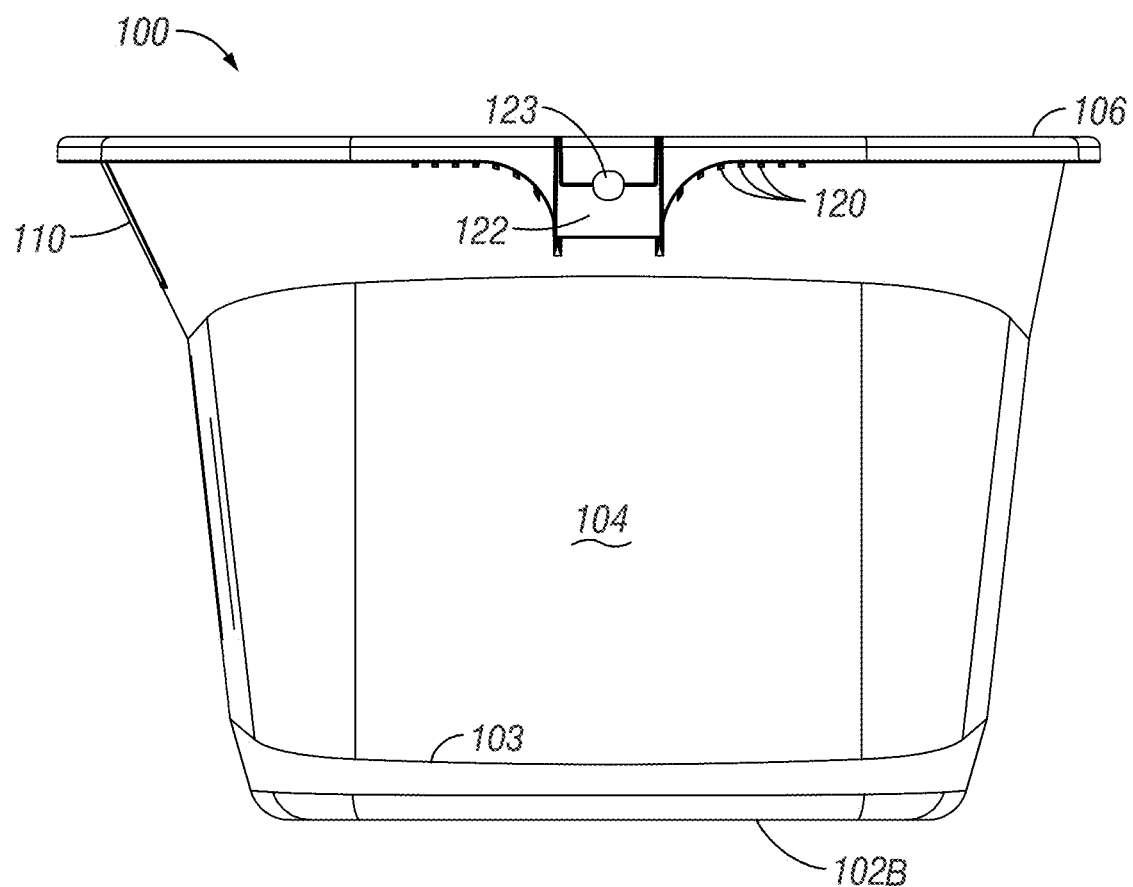
FIG. 10 shows a right-side elevational view thereof.
Figure 11:
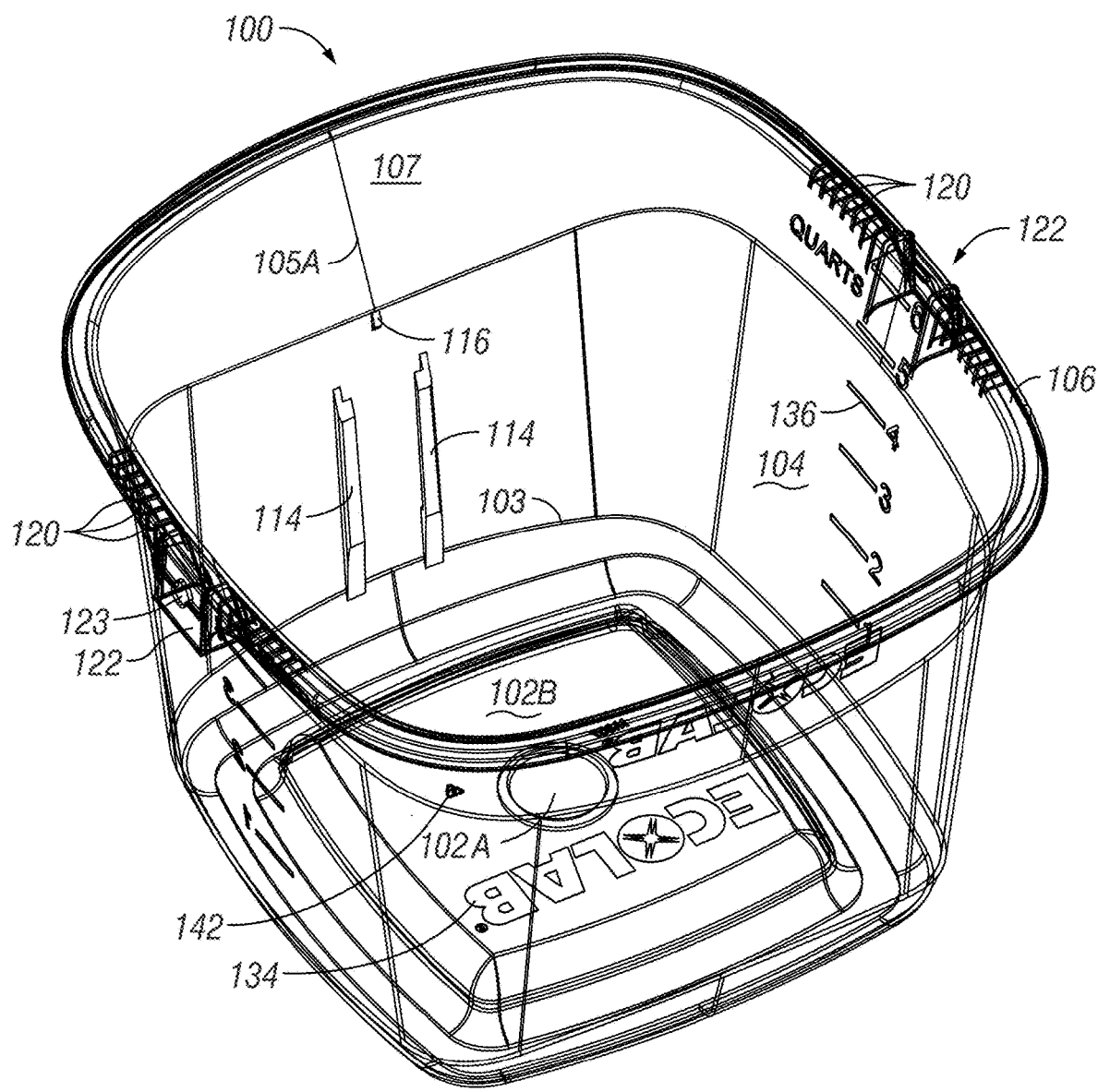
FIG. 11 shows a rear perspective view of a substantially transparent pail.
Figure 12:
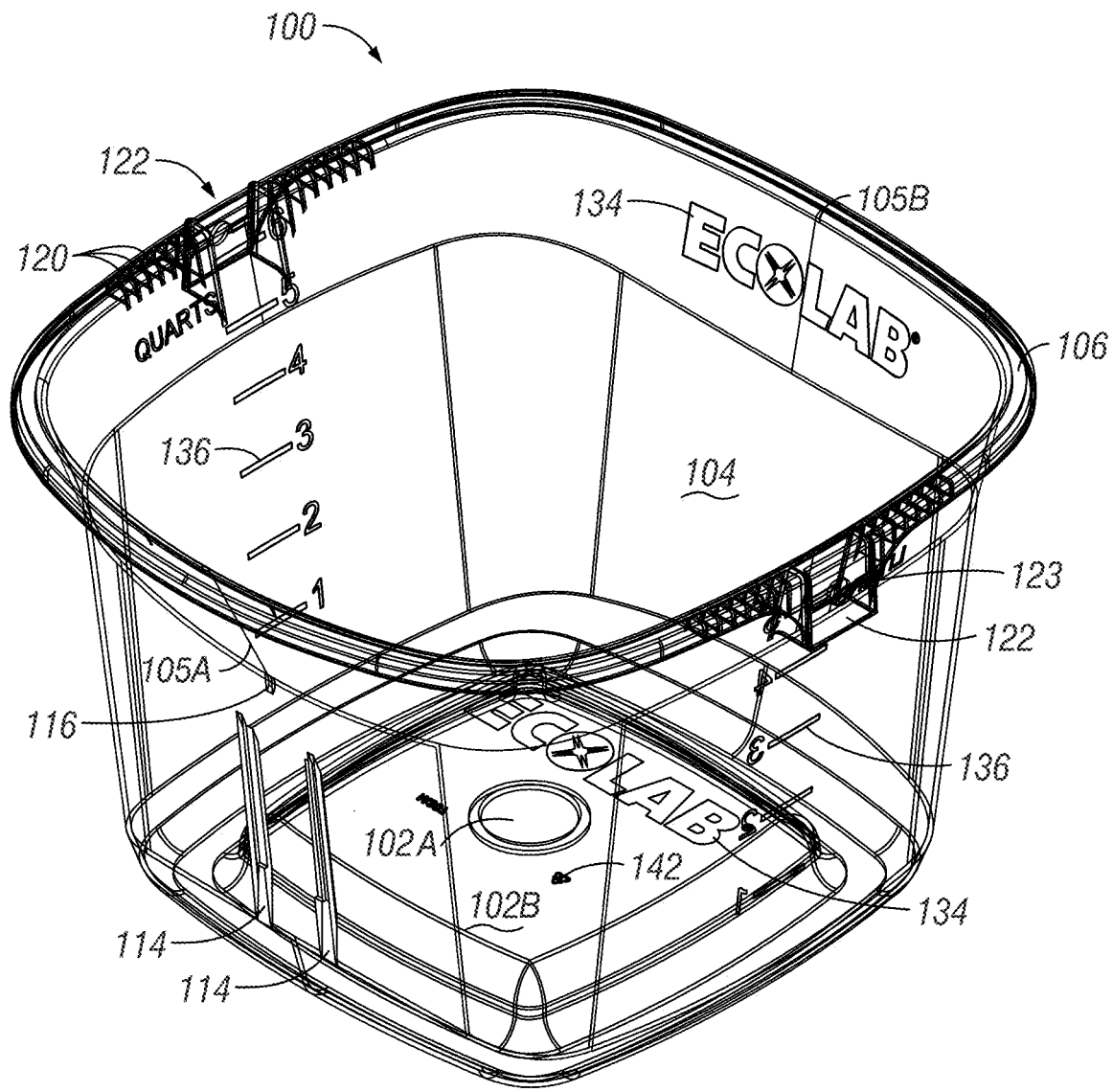
FIG. 12 shows a front perspective view thereof.
Figure 13:
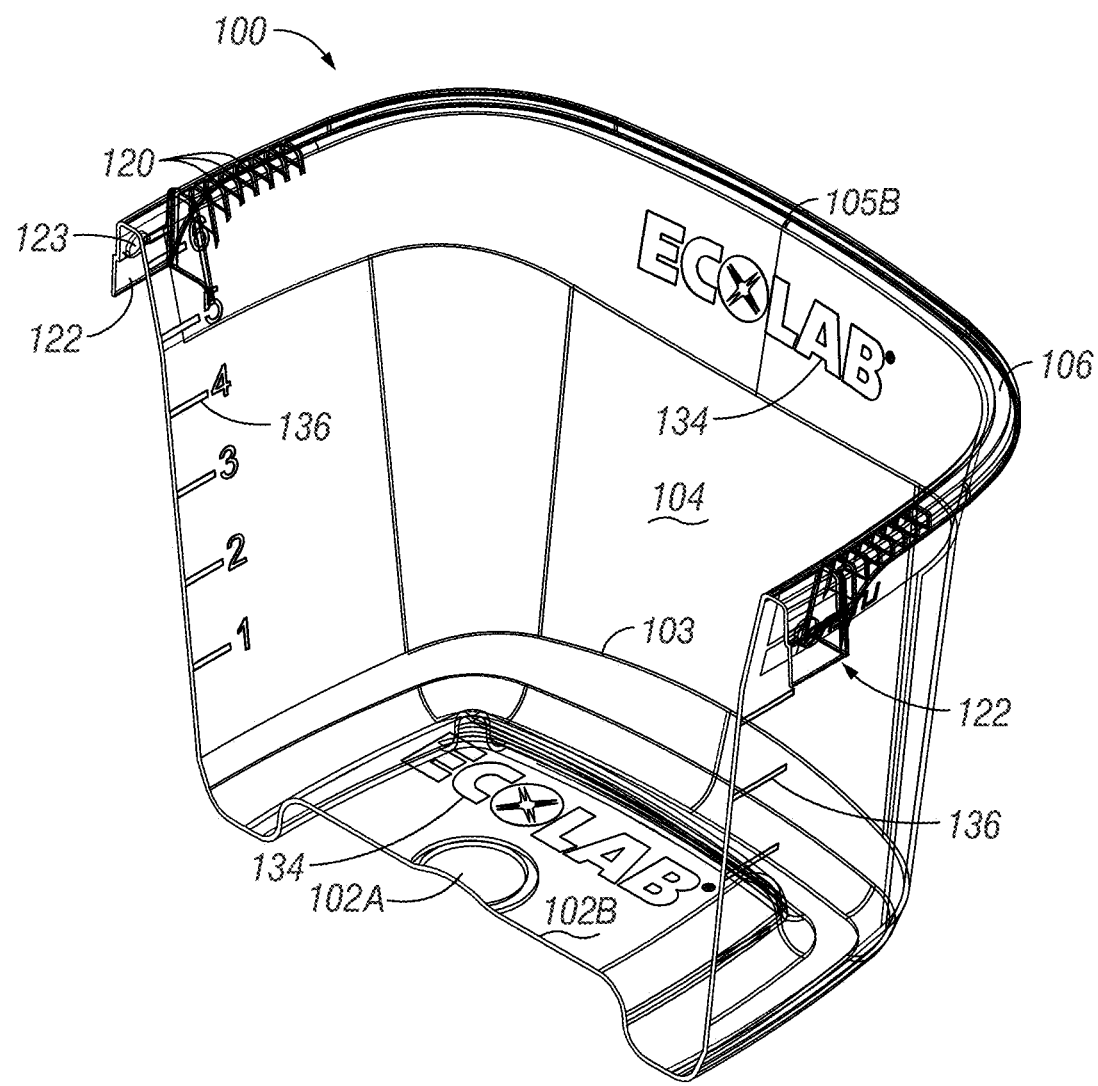
FIG. 13 shows an xz cross-sectional perspective view thereof.
Figure 14:
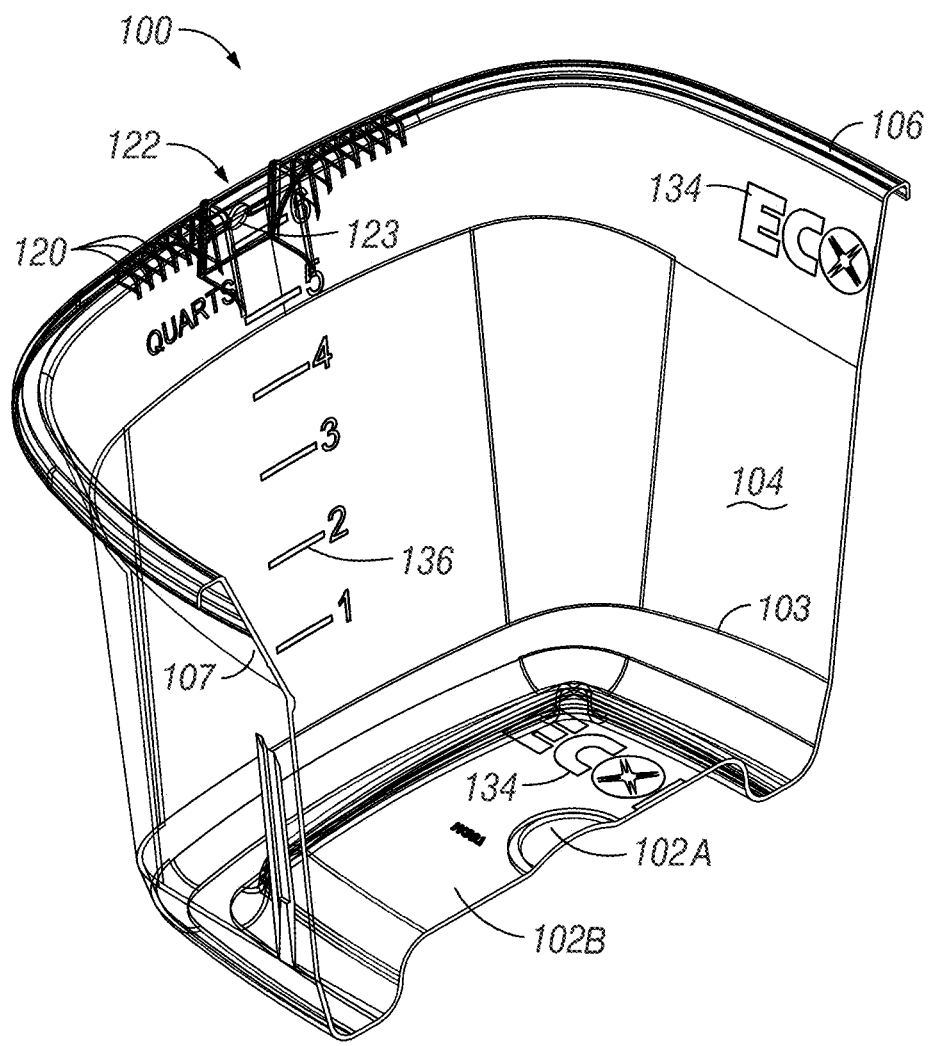
FIG. 14 shows an xy cross-section perspective view thereof.
Figure 15:
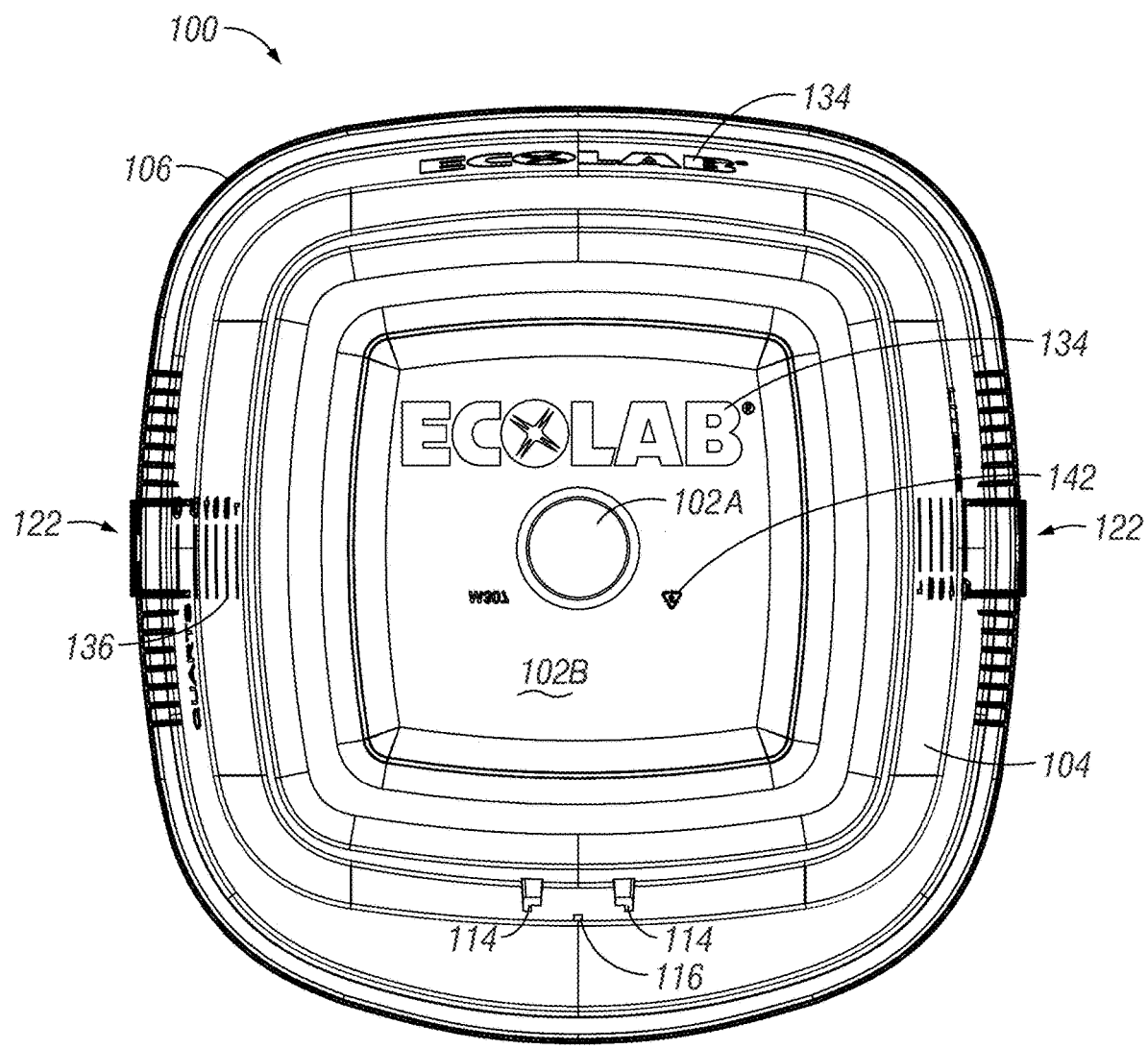
FIG. 15 shows a top elevational view thereof.
Figure 16:
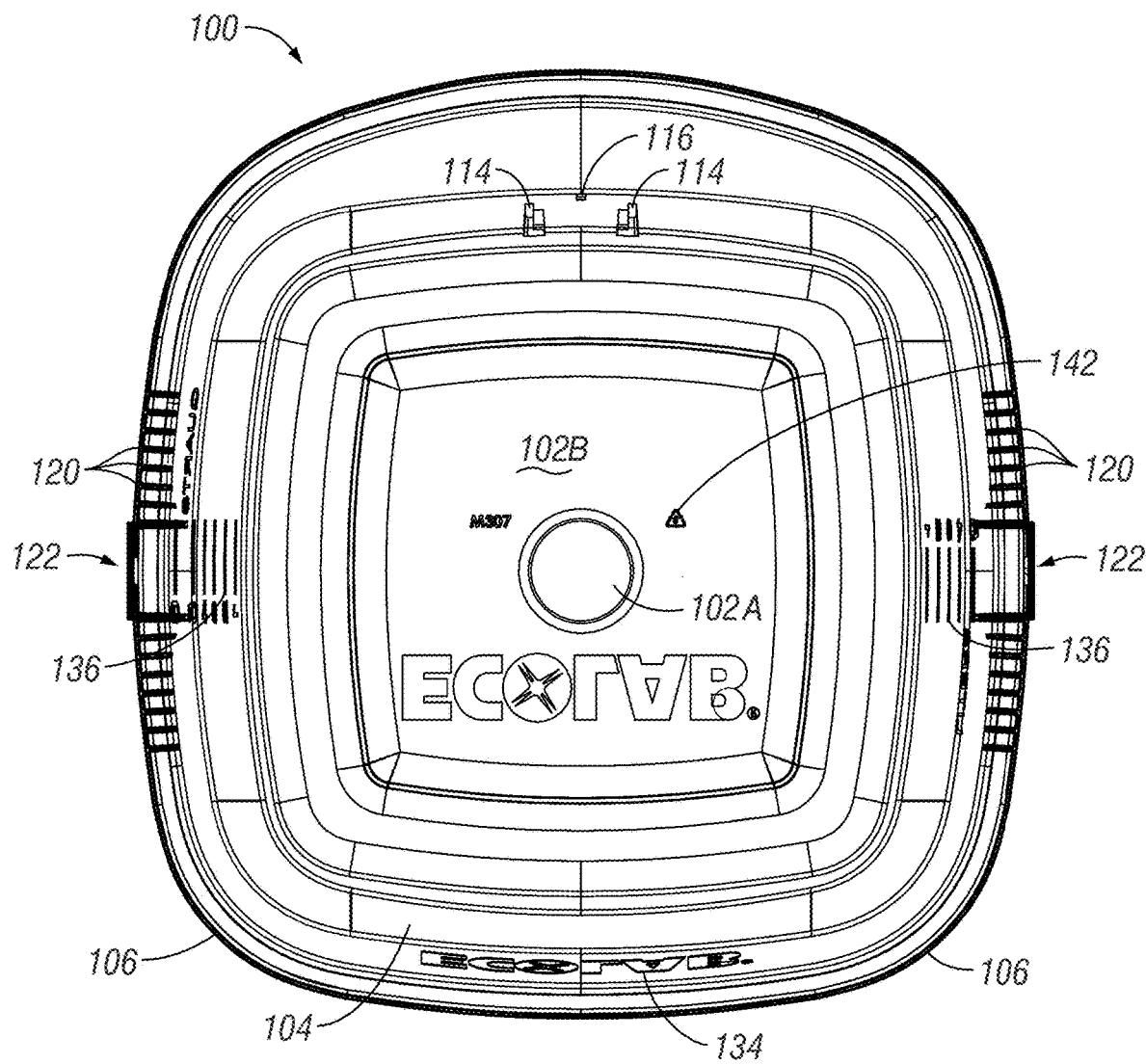
FIG. 16 shows a bottom elevational view thereof.
Figure 17:
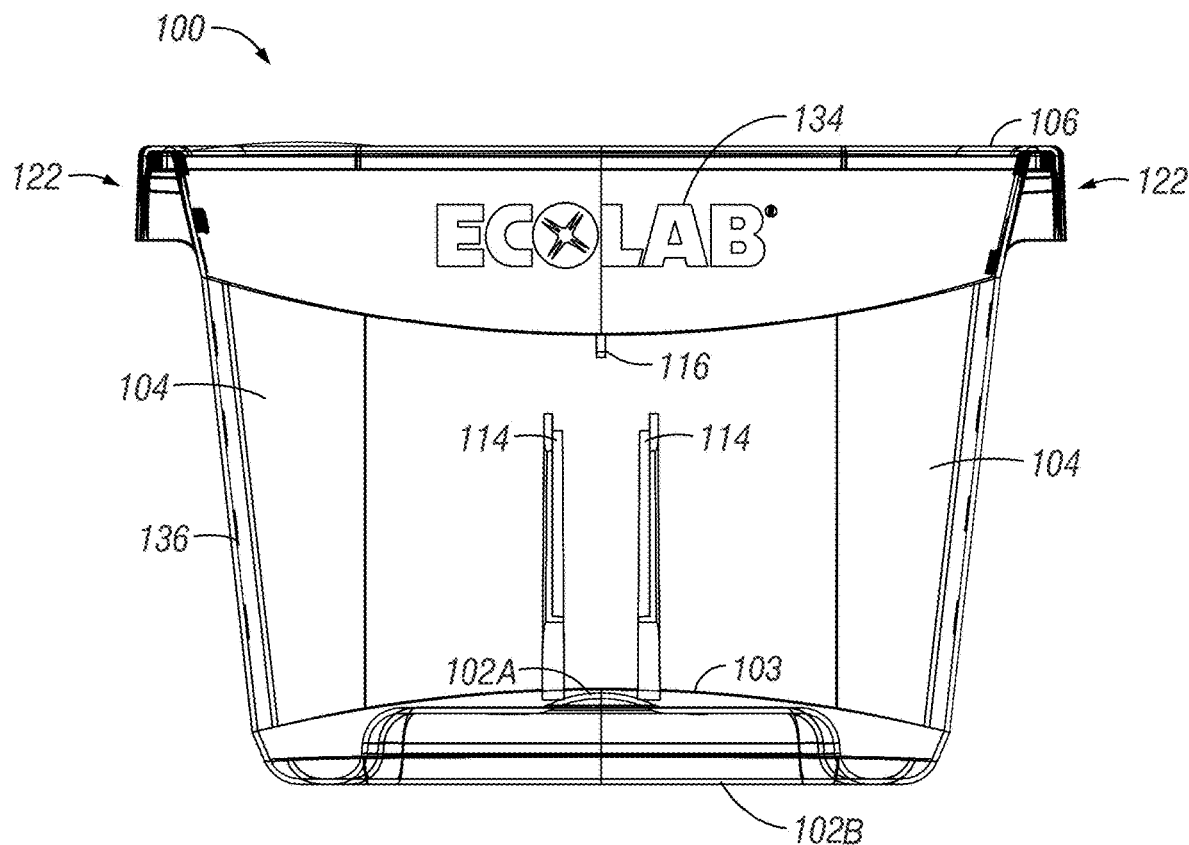
FIG. 17 shows a front elevational view thereof.
Figure 18:
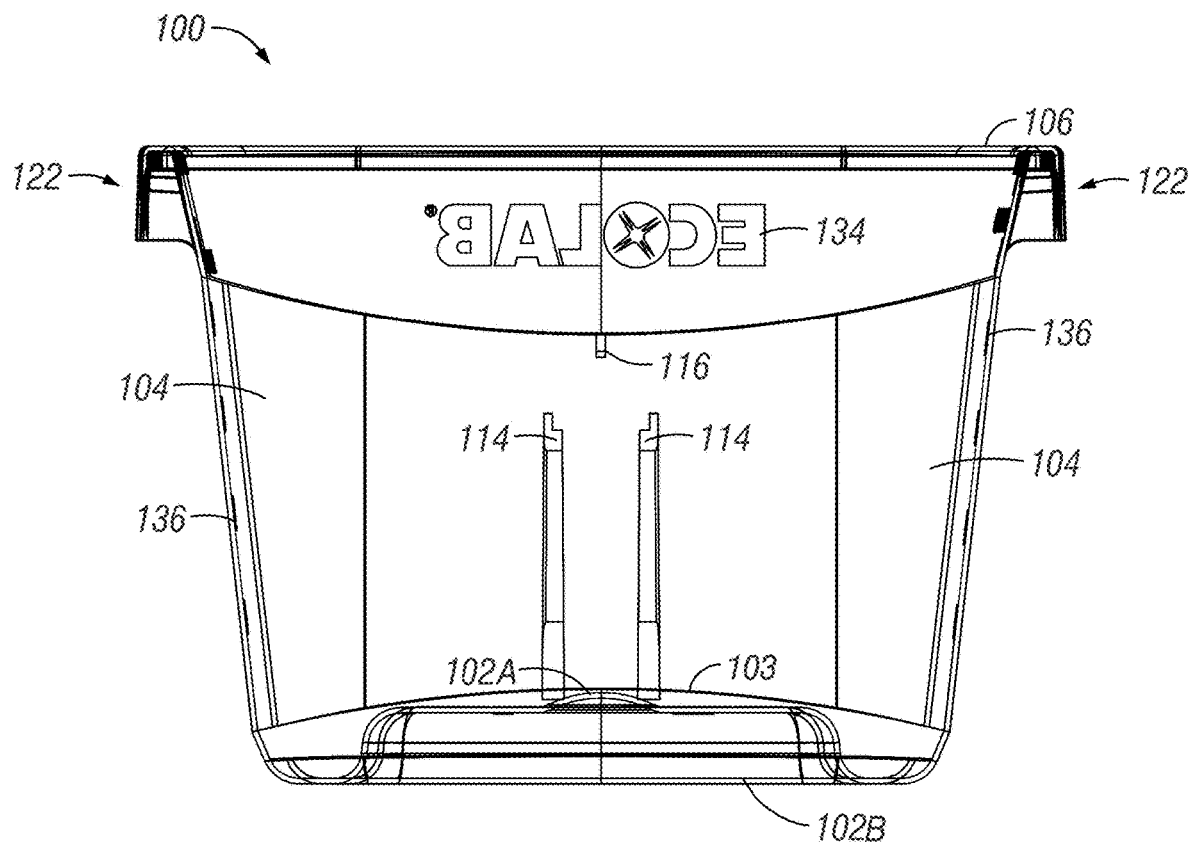
FIG. 18 shows a rear elevational view thereof.
Figure 19:
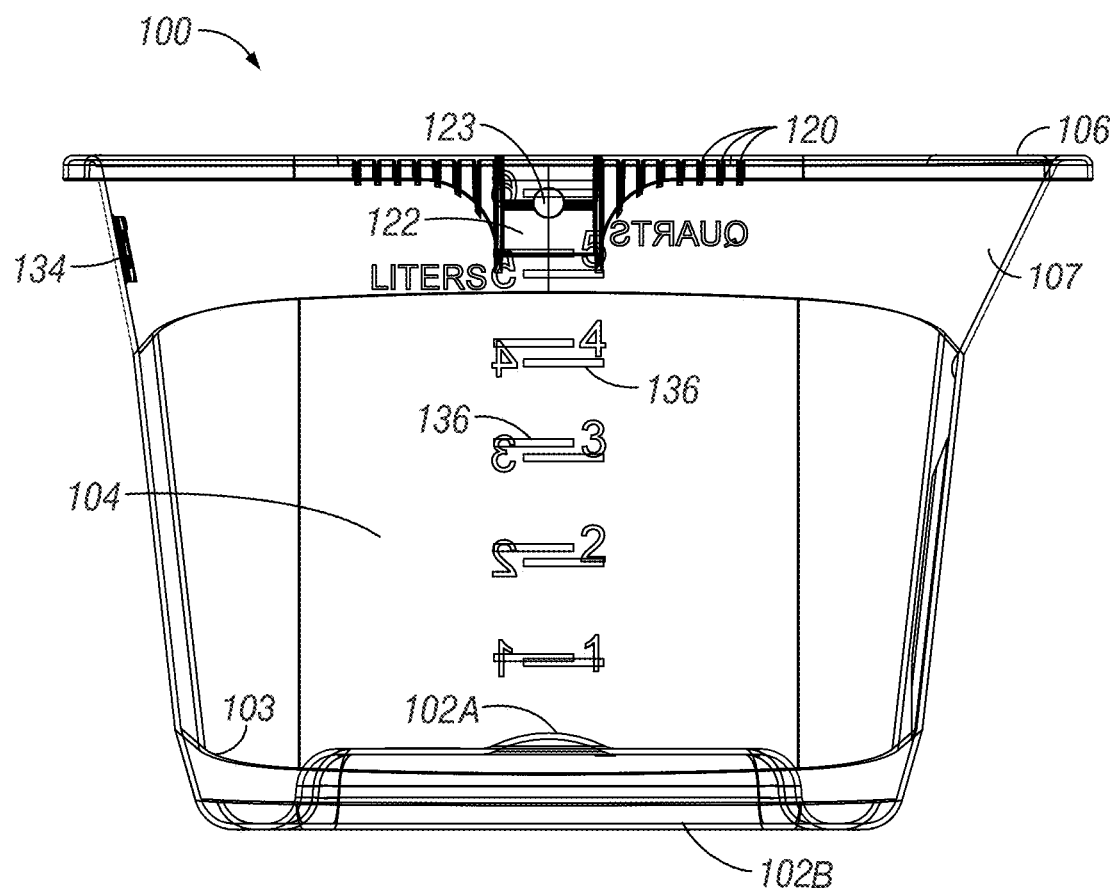
FIG. 19 shows a left-side elevational view thereof.
Figure 20:
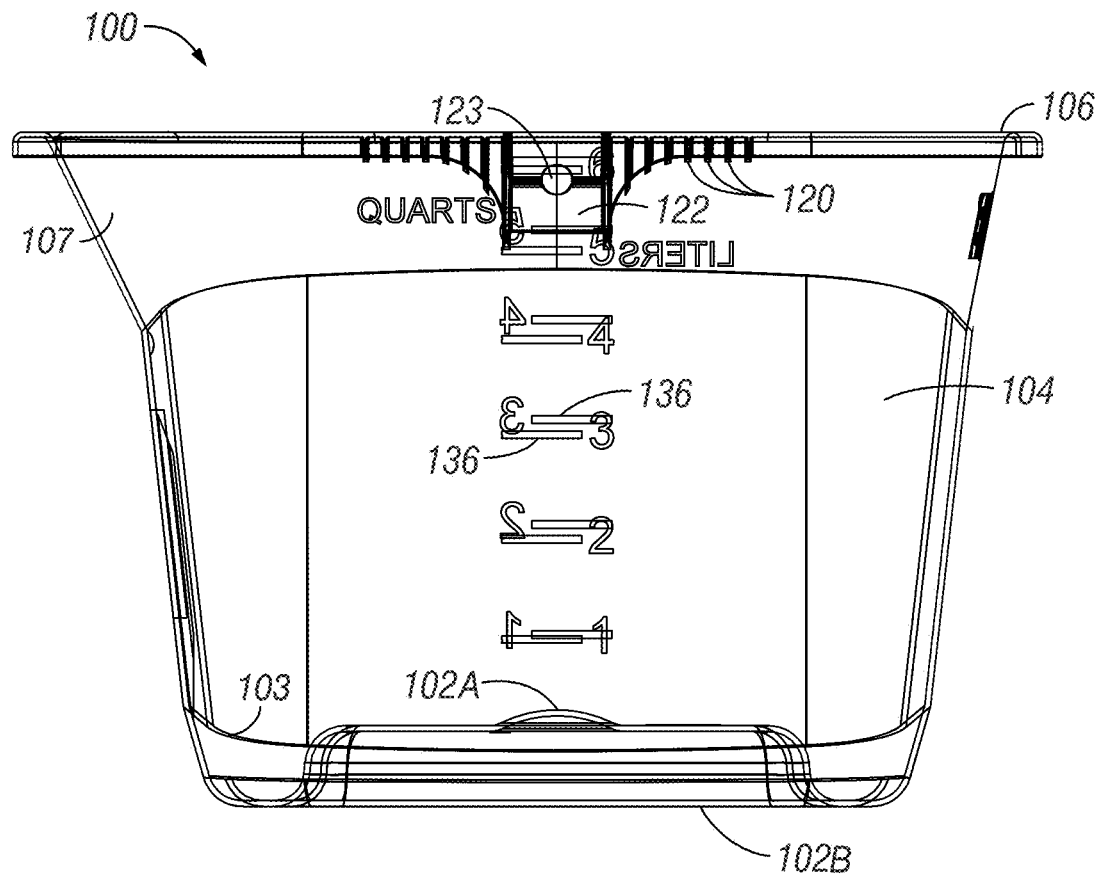
FIG. 20 shows a right-side elevational view thereof.

Various embodiments of the pH sensitive color indicators and their methods of manufacture and use will be described in detail with reference to the figures, wherein like reference numerals represent like parts throughout the several views. Reference to various embodiments does not limit the scope of the inventions. Figures represented herein are not limitations to the various embodiments according to the invention and are presented for exemplary illustration of the invention.

DETAILED DESCRIPTION OF THE PREFERRED EMBODIMENT

The present disclosure relates to pH sensitive color indicators for assessing the concentration of a cleaning composition, in particular, sanitizing and/or disinfecting compositions. The disclosure also describes methods of making and using the pH sensitive color indicating products.

It should be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form.

Numeric ranges recited within the specification are inclusive of the numbers defining the range and include each integer within the defined range. Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges, fractions, and individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6, and decimals and fractions, for example, 1.2, 3.8, 1½, and 4¾. This applies regardless of the breadth of the range.

Definitions

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The term "about," as used herein, refers to variation in the numerical quantity that can occur, for example, through typical measuring techniques and equipment, with respect to any quantifiable variable, including, but not limited to, mass, volume, time, temperature, pH, and log count of bacteria or viruses. Further, given solid and liquid handling procedures used in the real world, there is certain inadvertent error and variation that is likely through differences in the manufacture, source, or purity of the ingredients used to make the compositions or carry out the methods and the like. The term "about" also encompasses these variations. Whether or not modified by the term "about," the claims include equivalents to the quantities.

The methods and compositions of the present invention may comprise, consist essentially of, or consist of the components and ingredients of the present invention as well as other ingredients described herein. As used herein, "consisting essentially of" means that the methods, systems, apparatuses and compositions may include additional steps, components or ingredients, but only if the additional steps, components or ingredients do not materially alter the basic and novel characteristics of the claimed methods, systems, apparatuses, and compositions.

The term "actives" or "percent actives" or "percent by weight actives" or "actives concentration" are used interchangeably herein and refers to the concentration of those ingredients involved in cleaning expressed as a percentage minus inert ingredients such as water or salts. It is also sometimes indicated by a percentage in parentheses, for example, "chemical (10%)."

As used herein, the term "alkyl" or "alkyl groups" refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups).

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups.

In some embodiments, substituted alkyls can include a heterocyclic group. As used herein, the term "heterocyclic group" includes closed ring structures analogous to carbocyclic groups in which one or more of the carbon atoms in the ring is an element other than carbon, for example, nitrogen, sulfur or oxygen. Heterocyclic groups may be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan.

As used herein, the term "soil" or "stain" refers to any soil, including, but not limited to, non-polar oily and/or hydrophobic substances which may or may not contain particulate matter such as industrial soils, mineral clays, sand, natural mineral matter, carbon black, graphite, kaolin, environmental dust, and/or food based soils such as blood, proteinaceous soils, starchy soils, fatty soils, cellulosic soils, etc.

As used herein, the term "antimicrobial" refers to a compound or composition that reduces and/or inactivates a microbial population, including, but not limited to bacteria, viruses, fungi, and algae within about 10 minutes or less, about 8 minutes or less, about 5 minutes or less, about 3 minutes or less, about 2 minutes or less, about 1 minute or less, or about 30 seconds or less. Preferably, the term antimicrobial refers to a composition that provides at least about a 3-log, 3.5 log, 4 log, 4.5 log, or 5 log reduction of a microbial population in about 10 minutes or less, about 8 minutes or less, about 5 minutes or less, about 3 minutes or less, about 2 minutes or less, about 1 minute or less, or about 30 seconds or less.

As used herein, the term "sanitizer" refers to an agent that reduces the number of bacterial contaminants to safe levels as judged by public health requirements. In an embodiment, sanitizers for use in this invention will provide at least a 99.999% reduction (5-log order reduction). These reductions can be evaluated using a procedure set out in *Germicidal and Detergent Sanitizing Action of Disinfectants*, Official Methods of Analysis of the Association of Official Analytical Chemists, paragraph 960.09 and applicable sections, 15th Edition, 1990 (EPA Guideline 91-2). According to this reference a sanitizer should provide a 99.999% reduction (5-log order reduction) within 30 seconds at room temperature, 25±2° C., against several test organisms.

As used herein, the term "cleaning" refers to a method used to facilitate or aid in soil removal, bleaching, microbial population reduction, and any combination thereof. As used herein, the term "microorganism" refers to any noncellular or unicellular (including colonial) organism. Microorganisms include all prokaryotes. Microorganisms include bacteria (including cyanobacteria), spores, lichens, fungi, protozoa, virinos, viroids, viruses, phages, and some algae. As used herein, the term "microbe" is synonymous with microorganism.

As used herein, the phrase "food processing surface" refers to a surface of a tool, a machine, equipment, a structure, a building, or the like that is employed as part of a food processing, preparation, or storage activity. Examples of food processing surfaces include surfaces of food processing or preparation equipment (e.g., slicing, canning, or transport equipment, including flumes), of food processing wares (e.g., utensils, dishware, wash ware, and bar glasses), and of floors, walls, or fixtures of structures in which food processing occurs. Food processing surfaces are found and employed in food anti-spoilage air circulation systems, aseptic packaging sanitizing, food refrigeration and cooler cleaners and sanitizers, ware washing sanitizing, blancher cleaning and sanitizing, food packaging materials, cutting board additives, third-sink sanitizing, beverage chillers and warmers, meat chilling or scalding waters, autodish sanitizers, sanitizing gels, cooling towers, food processing antimicrobial garment sprays, and non-to-low-aqueous food preparation lubricants, oils, and rinse additives.

The term "hard surface" refers to a solid, substantially non-flexible surface such as a counter top, tile, floor, wall, panel, window, plumbing fixture, kitchen and bathroom furniture, appliance, engine, circuit board, dish, mirror, window, monitor, touch screen, and thermostat. Hard surfaces are not limited by the material; for example, a hard surface can be glass, metal, tile, vinyl, linoleum, composite, wood, plastic, etc. Hard surfaces may include for example, health care surfaces and food processing surfaces.

As used herein, the phrase "health care surface" refers to a surface of an instrument, a device, a cart, a cage, furniture, a structure, a building, or the like that is employed as part of a health care activity. Examples of health care surfaces include surfaces of medical or dental instruments, of medical or dental devices, of electronic apparatus employed for monitoring patient health, and of floors, walls, or fixtures of structures in which health care occurs. Health care surfaces are found in hospital, surgical, infirmity, birthing, mortuary, and clinical diagnosis rooms. These surfaces can be those typified as "hard surfaces" (such as walls, floors, bed-pans, etc.,), or fabric surfaces, e.g., knit, woven, and non-woven surfaces (such as surgical garments, draperies, bed linens, bandages, etc.,), or patient-care equipment (such as respirators, diagnostic equipment, shunts, body scopes, wheel chairs, beds, etc.,), or surgical and diagnostic equipment. Health care surfaces include articles and surfaces employed in animal health care.

As used herein, the term "instrument" refers to the various medical or dental instruments or devices that can benefit from cleaning with a composition according to the present invention.

As used herein, the phrases "medical instrument," "dental instrument," "medical device," "dental device," "medical equipment," or "dental equipment" refer to instruments, devices, tools, appliances, apparatus, and equipment used in medicine or dentistry. Such instruments, devices, and equipment can be cold sterilized, soaked or washed and then heat sterilized, or otherwise benefit from cleaning in a composition of the present invention. These various instruments, devices and equipment include, but are not limited to: diagnostic instruments, trays, pans, holders, racks, forceps, scissors, shears, saws (e.g. bone saws and their blades), hemostats, knives, chisels, rongeurs, files, nippers, drills, drill bits, rasps, burrs, spreaders, breakers, elevators, clamps, needle holders, carriers, clips, hooks, gouges, curettes, retractors, straightener, punches, extractors, scoops, keratomes, spatulas, expressers, trocars, dilators, cages, glassware, tubing, catheters, cannulas, plugs, stents, scopes (e.g., endoscopes, stethoscopes, and arthroscopes) and related equipment, and the like, or combinations thereof.

As used herein, the term "microorganism" refers to any noncellular or unicellular (including colonial) organism. Microorganisms include all prokaryotes. Microorganisms include bacteria (including cyanobacteria), spores, lichens, fungi, protozoa, virinos, viroids, viruses, phages, and some algae. As used herein, the term "microbe" is synonymous with microorganism.

As used herein, the term "soft surface" refers to surfaces not classified as hard surfaces, but which are solid surfaces. Soft surfaces, include, but are not limited to, textiles, fabrics, woven surfaces, and non-woven surfaces. Soft surfaces, include, but are not limited to, carpet, curtains, fabrics, hospital partitions, linens, and upholstery.

As used herein, the term "substantially free" refers to compositions completely lacking the component or having such a small amount of the component that the component does not affect the performance of the composition. The component may be present as an impurity or as a contaminant and shall be less than 0.5 wt-%. In another embodiment, the amount of the component is less than 0.1 wt-% and in yet another embodiment, the amount of component is less than 0.01 wt-%.

The term "virus", as used herein refers to a type of microorganism that can include both pathogenic and non-pathogenic viruses. Pathogenic viruses can be classified into two general types with respect to the viral structure: enveloped viruses and non-enveloped viruses. Some well-known enveloped viruses include herpes virus, influenza virus; paramyxovirus, respiratory syncytial virus, corona virus, HIV, hepatitis B virus, hepatitis C virus and SARS-CoV virus. Non-enveloped viruses, sometimes referred to as "naked" viruses, include the families Picornaviridae, Reoviridae, Caliciviridae, Adenoviridae and Parvoviridae. Members of these families include rhinovirus, poliovirus, adenovirus, hepatitis A virus, norovirus, papillomavirus, and rotavirus. It is known in the art that "enveloped" viruses are relatively sensitive and, thus, can be inactivated by commonly used disinfectants. In contrast, non-enveloped viruses are substantially more resistant to conventional disinfectants and are significantly more environmentally stable than enveloped viruses.

As used herein, the term "ware" refers to items such as eating and cooking utensils, dishes, and other hard surfaces such as showers, sinks, toilets, bathtubs, countertops, windows, mirrors, transportation vehicles, and floors. As used herein, the term "warewashing" refers to washing, cleaning, or rinsing ware. Ware also refers to items made of plastic. Types of plastics that can be cleaned with the compositions according to the invention include but are not limited to, those that include polypropylene polymers (PP), polycarbonate polymers (PC), melamine formaldehyde resins or melamine resin (melamine), acrylonitrile-butadiene-styrene polymers (ABS), and polysulfone polymers (PS). Other exemplary plastics that can be cleaned using the compounds and compositions of the invention include polyethylene terephthalate (PET) polystyrene polyamide.

The terms "water soluble" and "water dispersible" as used herein, means that the ingredient is soluble or dispersible in water in the inventive compositions. In general, the ingredient should be soluble or dispersible at 25° C. concentration of between about 0.1 wt. % and about 15 wt. % of the water, more preferably at a concentration of between about 0.1 wt. % and about 10 wt. %.

The term "weight percent," "wt. %," "wt-%," "percent by weight," "% by weight," and variations thereof, as used herein, refer to the concentration of a substance as the weight of that substance divided by the total weight of the composition and multiplied by 100.

pH Sensitive Color Indicators

The present disclosure relates to pH sensitive color indicators for assessing the concentration of a cleaning composition, in particular, sanitizing and/or disinfecting compositions. The disclosure also describes methods of making and using the pH sensitive color indicating products. We have found that there is a correlation in the pH and effectiveness of certain new types of sanitizers and disinfectants, in particular, acid anionic cleaning compositions. Thus, while traditional mechanisms for assessing whether a necessary concentration of active sanitizing or disinfecting agent has been to measure the concentration of active ingredient, we have found that the necessary concentration of active ingredient in acid anionic cleaners can be evaluated by determining the pH of a composition, which is related to the concentration of the active ingredient. We determined that use of pH sensitive color indicators could overcome many of the aforementioned difficulties and problems existing in this art. Although some pH sensitive color indicators do currently exist, those in existence suffer many problems making them difficult to use. For example, existing pH sensitive color indicators are require immersion (of a test strip) or addition (of a use solution) to a vial of test chemical for a set amount of time such as 5 seconds, required reading of the result within 10 seconds at a set temperature, and a required comparison to a standard where colors and hues must be compared within that 10 second period before the results may no longer be viable. Such methods are difficult to employ in the field due to differences in conditions such as temperature and the requirement that results be read and determined within set amounts of time. Further, such methods are irreversible and thus not continual and in real-time where changes to the compositions can be readily monitored over a time period without the need to retest.

In particular, by using a pH sensitive color indicator, the need for expensive and/or complicated equipment used to measure the active cleaning components in a composition (such as chlorine or quaternary ammonium) are not necessary. Further, there is no need to analyze and interpret test results to evaluate the suitability of a particular concentration. Rather the use of pH sensitive color indicators can provide an image or color change at-a-glance to signal that a concentration is sufficient or insufficient for the desired cleaning application, i.e., whether the concentration is sufficient for sanitizing or disinfecting.

The pH sensitive color indicators comprise a pH sensitive dye bound to a substrate to allow for visual indication of the concentration of a cleaning composition. A color change or appearance of an image can indicate that a composition is either in or out of the required concentration to achieve a particular antimicrobial activity. Thus, the pH sensitive color indicators can provide an at-a-glance real-time determination of a composition's sanitizing and/or disinfecting efficacy.

In a preferred embodiment, the pH sensitive color indicator can comprise a dye and a substrate.

Dye

The pH sensitive color indicators comprise a pH sensitive dye. Preferably the dye comprises an azo dye. The dye employed can be a combination or mixture of dyes including mixtures comprised of two azo dyes, three azo dyes, four azo dyes, or more. Azo dyes are organic compounds comprising one or more diazenyl functional groups:

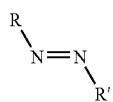

wherein R and R' are either an aryl group or an alkyl group. Preferred azo dyes include those where R has between 2 and 20 carbons, more preferably between 4 and 16 carbons, and where R' has between 2 and 20 carbons, more preferably between 4 and 16 carbons. For a more detailed description of suitable azo dyes, see U.S. Pat. No. 4,029,598 at column 2, line 7 through column 5, line 68, which is incorporated herein by reference in its entirety.

Preferred azo dyes include, but are not limited to, allura red AC, azo violet, basic red 18, bromothymol blue, Congo red, direct blue 1, direct brown 78, m-cresol purple, methyl orange, methyl red, para red, phenol red, reactive orange 16, tartrazine, thymol blue, xylenol blue, xylenol orange, and combinations or mixtures thereof.

In a preferred embodiment, the pH sensitive dye exhibits a color change at a pH of about 4.5 or less, at about 4.4 or less, at about 4.3 or less, at about 4.2 or less, at about 4.1 or less, about 4 or less, at about 3.9 or less, at about 3.8 or less, at about 3.7 or less, at about 3.6 or less, at about 3.5 or less, at about 3.4 or less, at about 3.2 or less, at about 3.1 or less, at about 3.0 or less, at about 2.9 or less, at about 2.8 or less, at about 2.7 or less, at about 2.6 or less, at about 2.5 or less, at about 2.4 or less, at about. 2.3 or less, at about 2.2 or less, at about 2.1 or less, or at about 2.0 or less. In a preferred embodiment, the pH sensitive dye exhibits a color change at a pH between about 2 and about 4.5, more preferably between about 2.2 and about 4.0, still more preferably between about 2.5 and about 3.5, or most preferably at a pH between about 2.8 and about 3.2. In a preferred embodiment, the pH sensitive dye has a pKa between about 2 and about 4.5, more preferably between about 2.2 and about 4, most preferably between about 2.5 and about 3.5.

Substrate

In an aspect of the invention, the azo dye is bound to or coated on a substrate such that in contact with a cleaning composition, the azo dye can change color on the substrate to indicate a sufficient or insufficient concentration for antimicrobial efficacy. The substrate can be any suitable substrate for a particular cleaning application. For example, the substrate can be, but is not limited to, a pail, a bucket, a dispenser, a spray bottle, a sprayer, a trigger sprayer, a sink, a coating, a liner, a mop, a paint, a paper, a sponge, a sticker, a towel, a window, or a wipe. The azo dye can be bound to or coated on the substrate. In a preferred embodiment, the substrate can be a paper having the azo dye bound or coated such that the dye exhibits a color change on the paper. In a preferred embodiment, the substrate can be adhered (or otherwise affixed) to a surface, wherein the surface is one or more of a plastic surface, a composite surface, a glass surface, or a metal surface. In a most preferred embodiment, the azo dye is bound to or coated on a cellulose-based substrate, wherein the cellulose-based substrate is adhered (or otherwise affixed) to a surface, and wherein that surface is removably attached to a container, a pail, a bucket, a dispenser, a bottle, a sprayer, or a sink.

FIGS. 1-23 show non-limiting example embodiments of a substrate comprising a container 100, such as a pail or bucket. The container 100 typically includes a base 102B with a centrally located concave lug 102A, sidewall(s) 104, and an upper rim 106. The external side of the base 102B acts as the surface through which the pail or bucket 100 can operatively rest on external surface(s). The base 102B can optionally include feet, to decrease the surface area in contact with said external surface(s). The at least one sidewall 104 forms an upstanding boundary 103 about the base 102B and extends generally vertically upward terminating in the upper rim 106 of the container 100. The at least one sidewall 104 can include sections having varying tapers 105A, 105B relative to a vertical plane. For example, an upper portion of the container 100 can include a greater outward taper 105A relative to vertical than the lower portion of the container 100, and the upper rim 106 of the container 100 can be configured to have a taper 105B relative to vertical greater than the upper and lower portions. The sidewall 104 can extend generally upwardly and outwardly to flare near the mouth 107 of the container 100 to aid in minimizing the amount of fluid spilled when filling the container 100 and to direct fluid from the bucket during pouring.

The sidewall 104 and base 102B together may preferably form a substantially cylindrical shape, however can be configured so as to take on any suitable or otherwise known three-dimensional shape. For example, the shape of the container 100 can be selected from the group consisting of cylinders, ellipsoids (including spheres), partial ellipsoids (including hemispheres), regular polyhedrons (including pyramids, cubes, etc.), irregular polyhedrons, cones, combinations thereof, and/or the like. The container 100 is preferably constructed from materials such a polypropylene for withstanding handling of the chemistries disclosed herein. Other thermoplastics, such as those commonly used in injection molding processes, can also be used. The sidewall 104 and base 102B may be solid, partially hollow, or mostly hollow, but should at least be thick enough to establish a sufficient strength for the container 100 so as to withstand impacts and abrasion over the course of repeated use.

The container 100 of FIGS. 1-10 includes a two-material design wherein most of the pail or bucket 100 is opaque and a minority portion, e.g. windows 108, 110 of the pail or bucket 100 is transparent. Suitable transparent materials for the windows 108, 110 can non-limitingly include glass, fiberglass, polycarbonates, and/or the like.

The windows 108 and 110 permit wide viewing angles into the container 100 from external locations. During operation of the container 100, a pH strip 112 having the advantages disclosed herein and/or labels identifying the chemistries contained within the container 100 may be placed between the flexible retaining arms 114 and one or more of the windows 108, 110. The flexible retaining arms 114 are rigid enough so as to secure the pH strip and/or labels in position during movement of the bucket, but should be deformable enough so as to allow users to remove and/or replace pH strips and/or labels between uses of the container 100, and so as to accommodate pH strips and/or labels of varying thicknesses. As shown generally in FIGS. 1-10, the pH strip 112 and/or product identifiers may be stored at a location adjacent the windows 108, 110 until placed the interior of the sidewall 104 of the container 100. During operation, the user will be able to view the pH strip 112 and/or product identifier inside the container 100 without having to see through the top of the same. To further hold the pH strip 112 in place, an upper holder 116 is positioned on the interior or uppermost portion of the sidewall 104 so as to stabilize the pH strip 112 while inserted into one or more of the retention arms 114 extending from a location just above where the sidewall 104 meets the base 102B of the container 100. The retaining arms 114 substantially extend from a location just above the base 102B to the upper holder 116 and provide a retention area between the retention arms 114 and the window 108, 110, where the pH strip 112 can be slid therebetween. The pH strip 112 can be slid into a position for viewing from a upward location and in a downward direction, can be slid into position laterally, and/or a combination of the aforementioned directions. Such a slidable connection can be established through the use of one or more suitable slidable elements, including: a friction fit on a slip (non-stick) surface, guides, tracks, piston(s), shaft(s), sleeve(s), collar(s), ball bearings, actuator(s), linkage(s), pivot(s), and/or the like. It is preferred that the slidable connection only allow the pH strip 112, retention arms 114, and/or upper holder 116 to slide in one dimension (i.e. linearly) with respect to the sidewall 104. Yet, it is to be appreciated some minor relief in a second dimension can be to mitigate wear, tear, or failure of slidable components and/or elements. To that end, oils, grease, lubricants, antistatic agents, and/or other non-viscous fluids or devices can be applied where wear and tear is expected to further mitigate the same over time.

While the retention arms 114 exert a force generally directed towards the window 108, 110, the force may be easily overcome by a user to slide the pH strip 112 between the retention arms 114 and window. However, the retention arms 38 include some elasticity to re-exert tension to press the badge in place. Furthermore, as shown FIGS. 21-22, the retention arm 114/upper holder 116 combination may be fastened or otherwise affixed to the sidewall 104 by rivets 118. Other methods and means of attaching the retention arm 114/upper holder 116 combination to the container 100 are also contemplated to be part of the invention. For example, the retention arm 114/upper holder 116 combination may be adhered or otherwise secured to the container 100 via adhesives, screws, snaps, Velcro®, and/or the like. It is also contemplated that the retention arm 114/upper holder 116 combination be molded or otherwise formed as part of the base 102B and/or sidewall 104 such that it is integrally one piece with the container 100. Therefore, the retention arm 114/upper holder 116 combination may comprise a material similar to the dispenser body, such as a thermoplastic or the like.

As shown in FIGS. 11-20, wherein each surface of the container 100 is almost fully transparent, the upper rim 106 of the container 100 can be reinforced with any number of intermediate support members 120. The intermediate support members bridge the sidewall 104 and a lower and outward portion of the upper rim 106. The upper rim 106 of the container 10 can curve downwardly and outwardly so as to be gripped by a user.

Figure 21:
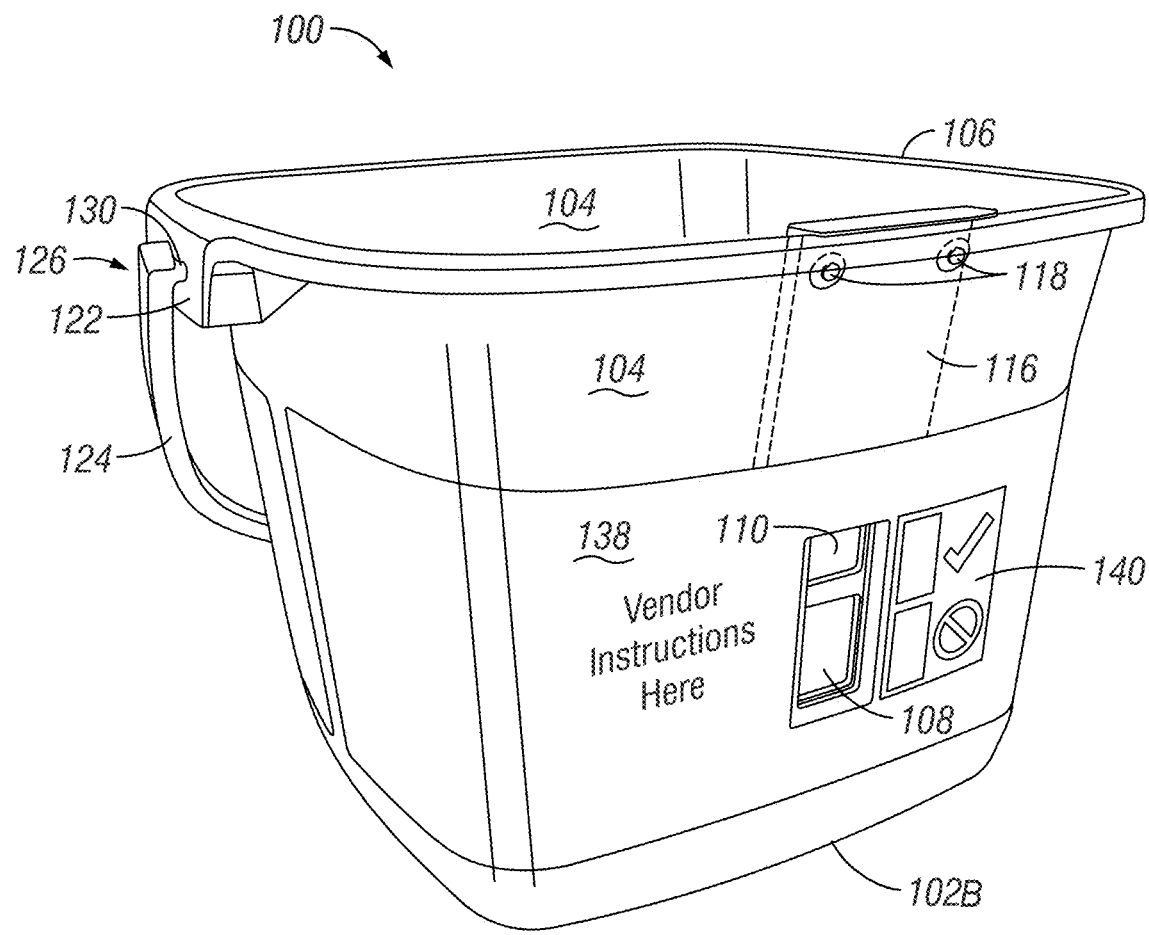
FIG. 21 shows a front, left-side perspective view of a substantially transparent pail with a substantially opaque sleeve and a plastic holder for a pH strip riveted thereto.
Figure 22:
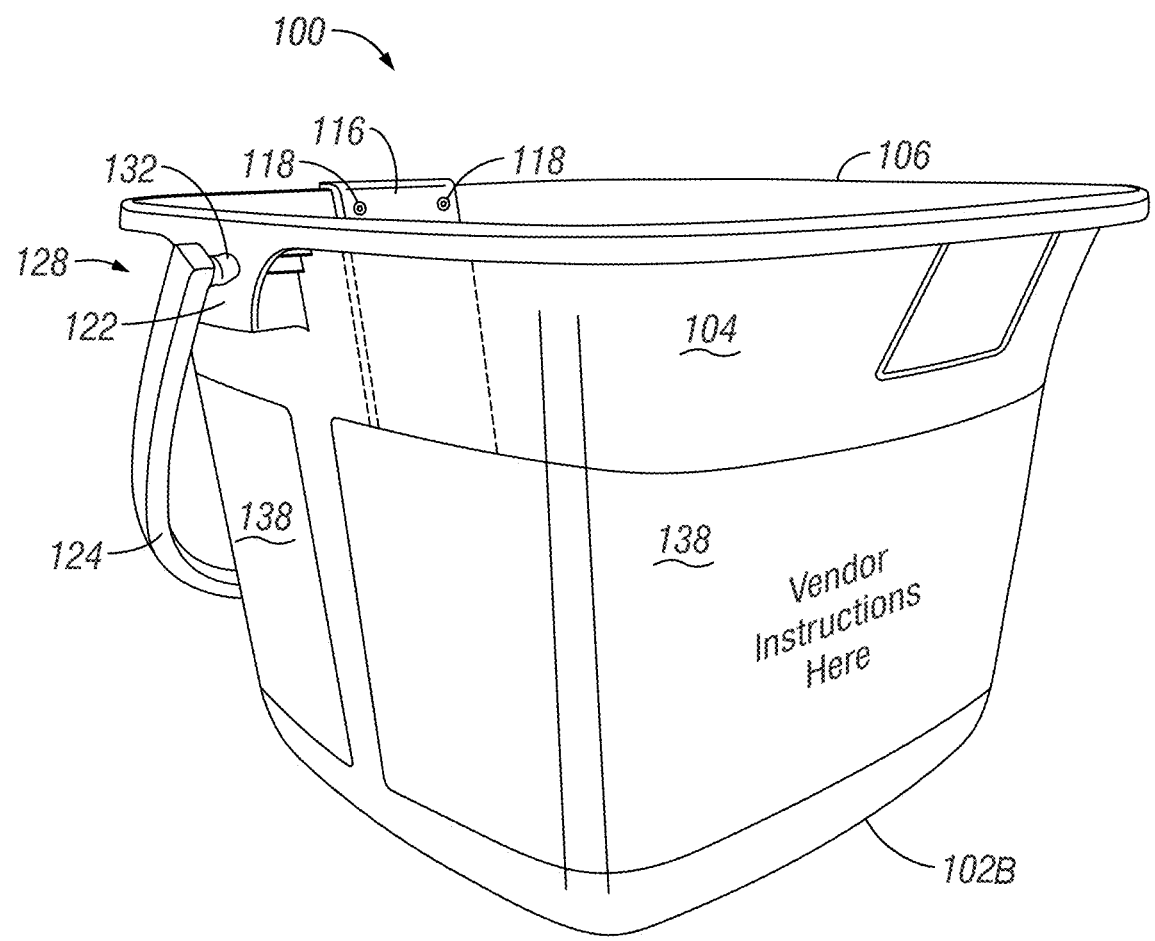
FIG. 22 shows a rear, right-side perspective view thereof.

Opposing portions of sidewall(s) 104 of the container 100 include ears 122 with apertures 123 positioned generally at the middle of the sidewall 104 and approximate the mouth of the container 100. The ears 122 can be positioned closer to the center of gravity of the container 100 to lessen the strain on the user when pouring liquids from the container 100. Furthermore, the ears 122 may be positioned off-center on the opposing sidewalls 104 to further aid in the ease of pouring liquids from the container 100. Each ear 122 is configured to receive posts 130 and 132 on respective ends 126 and 128 of the bail 124 as best illustrated in FIGS. 21-22. The posts 130 and 132 may be removably attached to the ears 122 on the container, or in a few embodiments, permanently attached thereto. It is preferred the posts 130 and 132 are pivotally attached to ears 122 via the apertures 123 on the container 100 which allows the bale 124 to pivot about the ears. Specifically, the bale 124 is permitted to freely rotate at least 180°, such as from an upstanding position to adjacent either sidewall 104 to any point therebetween. Mechanisms may be included on the container 100 so as to allow the bale 124 to be moved into pre-set interval positions such that the bail 124 cannot be dislodged therefrom unless the same mechanism or some other mechanism (e.g. a lock) is disabled or enough force is applied to the bale 124 to overcome the biasing force of the included mechanisms. The bale 124 is generally semicircular in shape and can optionally include a handle at the central, upper portion of an arc forming the semicircular shape.

As can also be seen in FIGS. 11-20, product source identifiers 134, liquid volume indicators 136, instructions for use 138, a legend 140 for the pH strip 112 (shown in FIGS. 21-23), and/or universal hazard symbols 142 can be made integral with and/or placed on the sidewalls 104 of the container 100 to facilitate quick identification of aspects related to the container 100 and/or the liquid intended to be stored and/or handled therein and/or dispensed therefrom, such as a sanitizer or other suitable cleaning agent. It is thus within the scope of the present invention that source identifiers, indicia, caution symbols, instructions, and/or other desirable identifying information made up of letters, numbers, graphics, markings, and/or other symbols be printed on the container 100. Any suitable process for doing so that is compatible with the material that the container 100 is manufactured of, such as a silk screen or photolithograph process or the like can be used. The indicia, instructions, and/or other identifying information can be raised (embossed), depressed, stamped, etched, written, labeled, painted, coated, or otherwise applied to internal and/or external portions of the base 102B and/or sidewall 104. Indicia can be applied to planar and non-planar surfaces.

The pH strip 112 and any azo dye contained therein can be bound to a number of different places which can be observed. For example, the azo dye can be bound to the interior of the bucket or pail 100 and viewed through the window 108, 110. In this aspect the bucket or pail 100 can be painted with a paint comprising the azo dye, the bucket material itself can have the azo dye bound to it, a sticker can be added to the interior of the bucket or pail 100 wherein the sticker comprises the azo dye, another object such as a plastic coupon, disc, or float comprising the azo dye or containing paint comprised of azo dye could be affixed to the bucket or pail 100, or the window can comprise the bound azo dye. While this embodiment is shown with a bucket/pail, it should be understood that according to the invention and present disclosure, this can be applied to any number of other substrates that can contain a cleaning composition, e.g., a spray bottle, a sprayer, a trigger sprayer, a liner, a dispenser, or a sink. In a preferred embodiment, the substrate can be coated and/or painted with a composition comprising the pH sensitive dye. In a preferred embodiment, the pH sensitive dye is in a non-water soluble paint, which is applied to a substrate.

Figure 23:
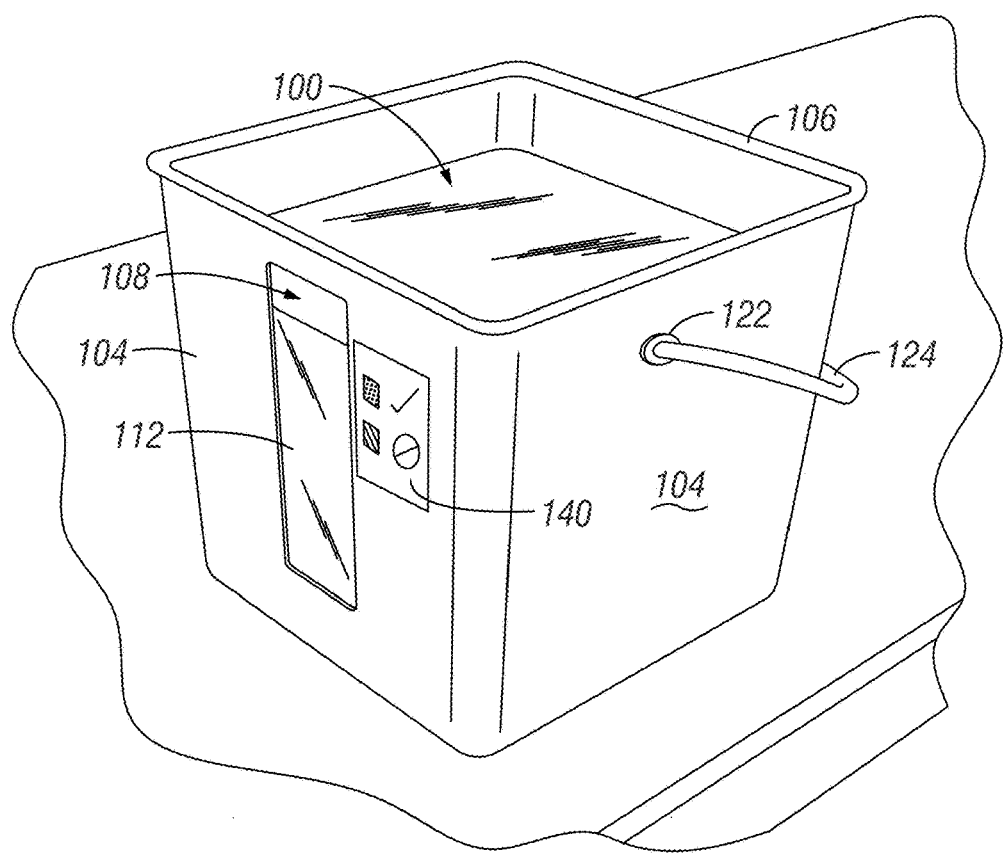
FIG. 23 shows a front, top perspective view of a bucket comprising a window, which is shown as a non-limiting example of a substrate comprising pH sensitive indicator.

The visual appearance of the pH strip 112 may thus be designed to aid in accomplishing the stated objectives for the present invention. For example, the pH strip 112 may be configured to show a color or several colors which contrast or are compatible with color(s) of adjacent object(s). The colors revealed may for example, comprise a primary color, secondary color, tertiary color, or any combination thereof. As shown in FIG. 23, the colors of the pH strip 112 can convey a particular meaning to a user. Caution might be indicated by a redder color and a warning may become visible if the pH falls out of a desirable range. A more uniform blue or green color might indicate a good solution. If the pH increases, the pH strip 112 may have more of a pinkish color. Where it is desired for the object to blend in with its surroundings, certain colors may be selected to produce a more camouflaged effect; substantially dark or substantially light colors might be selected to reduce or increase the likelihood of the object being noticed. Reflective elements may be added or subtracted from the pH strip 112 and/or container 100 to alter a reflectivity of the object. Furthermore, the visual appearance of the pH strip 112 and/or container 100 may be altered to provide a particular visual effect. Visual effects affect how an object appears to a person when looking at the object. Non-limiting examples of visual effects include changing the color of an object; increasing or decreasing color contrast between adjacent objects; and increasing or decreasing an object's reflectivity. In another aspect of the invention, a substrate used to apply a cleaning composition can comprise the bound azo dye. For example, a paper, a wipe, a towel, a sponge, a sprayer, a trigger sprayer, or a mop can comprise a bound azo dye. Suitable substrates can include, but are not limited to, plastics, metals, cellulose-based, or textiles. In this embodiment, the substrate once in contact with the cleaning composition can provide an indication as to whether the composition is efficacious for the particular cleaning application.

Methods of Preparation

The methods and techniques of preparing pH indicators can be produced in several ways, such as those described in U.S. Pat. No. 4,029,598 which is incorporated herein by reference in its entirety. Such techniques utilize a carrier, such as cellulose, and saturate the carrier with azo dyes having reactive groups capable of forming a chemical bond with the carrier material to form pH indicators that do not bleed. The methods include directly coloring a substrate, such as indicator paper comprising cellulose fibers during the manufacture thereof, by first suspending the paper raw material with water in suitable beaters, mixing the resultant suspension with an aqueous solution of the dye, and then making the suspension alkaline by the addition of bases for fixing the dye on the fiber. A second method involves imprinting a finished substrate, such as indicator paper, with a dye solution and fixing the dyes by a brief immersion into a warm alkaline fixing solution. By still another technique, the dye solution can be applied to a paper previously made alkaline, which after the application of the dye solution and a subsequent brief treatment in steam, is washed neutral and dried.

While the techniques and methods disclosed in U.S. Pat. No. 4,029,598 address the ability to produce non-bleeding pH indicators, they fail to address the ability to determine solution efficacy by a quick visual identification of color change using pH sensitive dyes. The disclosed methods producing non-bleeding pH indicators serve the purpose of providing a technician with more time to make comparisons with a color scale for a precise pH determination, but fail to utilize the color change as a quick indicator for solution efficacy. Further, these methods fail to address the color indicator properties on multiple substrates as will be discussed herein.

In a preferred embodiment, the pH sensitive dye is bound to the substrate in an amount between about 0.01 to about 0.1 grams of dye per 10 grams of bindable surface area of substrate. In an embodiment, the azo dye can comprise a fixative. Suitable fixatives include, but are not limited to, salts, acids, or bases.

Methods of Use

In a preferred embodiment, the pH sensitive dye can be used to indicate a positive or negative result regarding the efficacy of a cleaning composition for a desired application. For example, the pH indicator can change color to indicate that a cleaning composition has a pH at or below a maximum pH level for the efficacy of a particular antimicrobial activity such as sanitizing or disinfecting. By way of example only, and not limiting, where a composition provides an antimicrobial efficacy at a pH of about 3.2 or lower, an azo dye can be selected which exhibits a color change at a pH of about 3.2; this way if a composition has a pH of 3.2 or lower (i.e., it is efficacious for its particular application), it will change the color of the dye bound to the substrate indicating its efficacy; alternatively, if the cleaning composition is above 3.2 and not efficacious for its intended antimicrobial efficacy the color change will not be present when the composition is in contact with the pH sensitive dye.

In an aspect of the invention, the dye can be bound to the substrate in a pattern to reveal an image which signals a low enough pH for the composition to be efficacious. In this respect, the color itself is not critical but rather the revealing of the pattern or image.

A preferred embodiment comprises a method of detecting a concentration of a cleaning composition. The method can comprise contacting a cleaning composition with a pH sensitive indicator and determining whether the cleaning composition has a concentration efficacious for a cleaning application by observing whether the pH sensitive indicator exhibited a color change during or after the contacting step.

A preferred embodiment comprises a method of cleaning a surface. The method can comprise contacting a cleaning composition with a pH sensitive indicator and determining whether the cleaning composition has a concentration efficacious for a cleaning application by observing whether the pH sensitive indicator exhibited a color change during or after the contacting step and applying the cleaning composition to a surface if a color change was exhibited. The cleaning can be sanitizing or disinfecting the surface. If the composition does not affect a color change to the pH indicator, then the cleaning composition can be modified by adjusting the pH. The pH can be adjusted by increasing the concentration of the active cleaning composition components and/or by adding a pH modifier.

In a preferred embodiment, the compositions provide at least about a 3-log reduction of a microbial population, more preferably at least about a 3.5-log reduction, still more preferably equal to or greater than about 4-log reduction, even more preferably equal to or greater than about 4.5-log reduction, and most preferably equal to or greater than about 5-log reduction. Preferably, the cleaning compositions provide these reductions in about 30 minutes or less, about 20 minutes or less, about 15 minutes or less, about 10 minutes or less, about 5 minutes or less, about 4 minutes or less, about 3 minutes or less, about 2 minutes or less, about 90 seconds or less, about 60 seconds or less, even about 30 seconds or less.

Cleaning Compositions

In a preferred embodiment, the cleaning compositions compatible with the pH sensitive indicators are those having efficacy at a pH equal to or below about 4.5, more preferably equal to or below about 4, more preferably equal to or below about 3.5, still more preferably equal to or below about 3.2, yet more preferably equal to or less than about 3.0, and even more preferably equal to or less than about 2.8.

Antimicrobial Active

Such compositions can include peracid compositions, acid anionic compositions, or combinations or mixtures thereof. In a preferred embodiment, the cleaning composition comprises at least one anionic sulfonated or sulfated surfactant.

In a preferred embodiment, we have found that the desired concentration for sanitizing or disinfecting is between about 5 ppm and about 6000 ppm, more preferably between about 15 ppm and about 5000 ppm, and most preferably between about 100 ppm and about 4500 ppm. In such embodiments, the pH is preferably equal to or less than about 3.2, equal to or less than about 3.1, equal to or less than about 3.0, equal to or less than about 2.9, equal to or less than about 2.8.

Anionic surfactants are surface active substances which are categorized by the negative charge on the hydrophile; or surfactants in which the hydrophilic section of the molecule carries no charge unless the pH is elevated to the pKa or above (e.g. carboxylic acids). Carboxylate, sulfonate, sulfate and phosphate are the polar (hydrophilic) solubilizing groups found in anionic surfactants. Of the cations (counter ions) associated with these polar groups, sodium, lithium and potassium impart water solubility; ammonium and substituted ammonium ions provide both water and oil solubility; and, calcium, barium, and magnesium promote oil solubility.

Preferred anionic sulfonated surfactants include alkyl sulfonates, the linear and branched primary and secondary alkyl sulfonates, and the aromatic sulfonates with or without substituents. In an aspect, sulfonates include sulfonated carboxylic acid esters. In an aspect, suitable alkyl sulfonate surfactants include C8-C22 alkylbenzene sulfonates, or C10-C22 alkyl sulfonates. In an exemplary aspect, the anionic alkyl sulfonate surfactant is linear alkyl benzene sulfonic acid (LAS). In a preferred embodiment employing LAS as the anionic surfactant, the compositions are most effective at pH 3.5 or below. In a further embodiment, the anionic sulfonate surfactant may alternatively or additionally include diphenylated sulfonates, and/or sulfonated oleic acid.

Most preferred anionic sulfonated surfactants include, but are not limited to, C8-C22 alkylbenzene sulfonates, sulfonated oleic acid, a sulfosuccinate, a secondary alkane sulfonate, or mixtures thereof.

In an embodiment, the antimicrobial multi-purpose compositions of the present application may be substantially or entirely free of other surfactants including, amphoteric surfactants, cationic surfactants, nonionic surfactants, zwitterionic surfactants, or other anionic surfactants.

Buffering Agent

In some embodiments, the compositions can optionally comprise a buffering agent. In a preferred embodiment, the composition employs a pH buffering agent with a pKa between about 2 and about 3. If a buffering agent is included in the compositions, it can be in any suitable amount to buffer the composition at a desired pH. In a preferred embodiment, the concentrated antimicrobial multi-purpose composition comprises between about 0 wt. % and about 20 wt. %, more preferably between about 0.01 wt. % and about 15 wt. %, and most preferably between about 0.01 wt. % and about 10 wt. % of a buffering agent. In a preferred embodiment, the ready-to-use antimicrobial multi-purpose composition comprises between about 0 wt. % and about 3 wt. %, more preferably between about 0.01 wt. % and about 3 wt. %, and most preferably between about 0.01 wt. % and about 3 wt. % of a buffering agent. In a preferred embodiment, the buffering agent is in an amount less than about 0.5 wt. %, more preferably less than about 0.1 wt. %.

Preferred buffering agents include, but are not limited to, phosphonates, phosphonic acids, and/or phosphates. Exemplary buffering agents include a phosphonate salt(s) and/or a heterocyclic dicarboxylic acid, e.g., dipicolinic acid. In some embodiments, the buffering agent is pyridine carboxylic acid-based stabilizers, such as picolinic acid and salts, pyridine-2,6-dicarboxylic acid and salts, and phosphonate-based stabilizers, such as phosphoric acid and salts, pyrophosphoric acid and salts and most commonly 1-hydroxyethylidene-1,1-diphosphonic acid (HEDP) and salts. In other embodiments, the compositions and methods can comprise two or more buffering agents, e.g., HEDP and 2,6-pyridinedicarboxylic acid (DPA). Further, exemplary buffering agents include, but are not limited to, triethanol amine, imidazole, a carbonate salt, a phosphate salt, heterocyclic carboxylic acids, phosphonates, etc. In a preferred embodiment, the composition is free of a carboxylic acid buffering agent.

pH Modifiers

In some embodiments, the compositions can optionally include one or more pH modifiers to adjust pH and/or neutralize other ingredients. In a preferred embodiment, an alkaline pH modifier is added as an alkalizing agent. Preferably, an alkaline pH modifier is added to compositions comprising no chelant or a non-neutralized chelant. In a preferred embodiment, an acidic pH modifier is added to compositions comprising a neutralized chelant. In a preferred embodiment, an acidic pH modifier can be added as a coacidulant for disinfecting applications.

If a pH modifier is included in the compositions, it can be in any suitable amount to arrive at a desired pH. In a preferred embodiment, the concentrated antimicrobial multi-purpose composition comprises between about 0 wt. % and about 10 wt. %, more preferably between about 0.01 wt. % and about 8 wt. %, and most preferably between about 0.01 wt. % and about 5 wt. % of a pH modifier. In a preferred embodiment, the ready-to-use antimicrobial multi-purpose composition comprises between about 0 wt. % and about 10 wt. %, more preferably between about 0.01 wt. % and about 5 wt. %, and most preferably between about 0.01 wt. % and about 3 wt. % of a pH modifier.

Alkaline pH Modifier

The compositions may include one or more alkaline pH modifiers to adjust the compositions to a desired pH.

Suitable alkaline pH modifiers include, but are not limited to, one or more organic alkaline pH modifiers, one or more inorganic alkaline pH modifiers, or combinations thereof. Suitable organic alkaline pH modifiers include, but are not limited to, amines and strong nitrogen bases including, for example monoethanolamine, monopropanolamine, diethanolamine, dipropanolamine, triethanolamine, tripropanolamine, mixed isopropanolamines, and the like, or combinations thereof. Suitable inorganic alkaline pH modifiers include, but are not limited to, alkali metal hydroxides (e.g. sodium hydroxide, potassium hydroxide, or the like, or combinations thereof), alkali metal carbonates (e.g., sodium carbonate, potassium carbonate, sodium bicarbonate, potassium bicarbonate, sodium sesquicarbonate, potassium sesquicarbonate, and the like, or combinations thereof), alkali metal borates (e.g., sodium borate, potassium borate, and the like, or combinations thereof), alkali metal oxides (e.g., sodium oxide, potassium oxide, and the like, or combinations thereof), and the like, or combinations thereof. Examples of one or more alkaline pH modifiers include one or more of an alkanolamine and/or alkali metal carbonate.

A number of commercially available alkaline pH modifiers may be suitable for use in the antimicrobial multi-purpose compositions. Commercially available alkaline pH modifiers may include amino alcohols include, but are not limited to, primary amino alcohols (e.g. 2-Amino-2-methyl-1-propanol), amino alcohols (e.g. 2-Amino-2-methyl-1-propanol), commercially available alkyl alkanolamines including, but not limited to, monoethanolamine and triethanolamine.

In an aspect, the alkaline pH modifiers can include ethanolamines and/or carbonates. In a further preferred aspect, the alkaline pH modifiers include monoethanolamine, diethanolamine, triethanolamine, 2-amino-2-methyl-1-propanol, monoisopropanolamine, diisopropanolamine, 2-(2-Aminoethoxyl)ethanol (DGA) and/or an alkali metal carbonate. In a further preferred aspect, the alkaline pH modifiers do not include caustic, including for example, any alkali metal hydroxides. In still other preferred aspects, the alkaline pH modifiers do not include monoethanolamine, caustic and/or other highly alkaline components that result in an index value that require classification as a hazardous material, thereby requiring use of personal protective equipment (PPE) when handling the antimicrobial multi-purpose composition. In such preferred aspects, the alkaline pH modifiers monoethanolamine, caustic and/or other highly alkaline components are included at less than about 1 wt-% per component in a concentrate antimicrobial multi-purpose composition. In other aspects, such alkaline pH modifiers are excluded from the antimicrobial multi-purpose composition.

Acidic pH Modifier

The compositions may include an acidic pH modifier. In such an aspect, the acidic pH modifier can be a combination of a weak acid and a strong acid. Strong acids that can be used are acids which substantially dissociate an aqueous solution. "Weak" organic and inorganic acids are acids or acid components in which the first dissociation step of a proton from the acid moiety does not proceed essentially to completion when the acid is dissolved in water at ambient temperatures at a concentration within the range useful to form the present compositions.

Without wishing to be bound by theory, an acidic pH modifier is believed to affect the lipid envelope and/or capsid in the same manner. Moreover, the acidic pH modifiers disclosed herein facilitate the creation of a low pH buffer on the surface of a substrate, thereby prolonging the residual antimicrobial and antimicrobial activity of the compositions and products in which they are incorporated.

Exemplary strong acids suitable for use modifying the pH of the compositions include methane sulfonic acid, sulfuric acid, sodium hydrogen sulfate, phosphoric acid, phosphonic acid, nitric acid, sulfamic acid, hydrochloric acid, trichloroacetic acid, trifluoroacetic acid, toluene sulfonic acid, glutamic acid, and the like; alkane sulfonic acid, such as methane sulfonic acid, ethane sulfonic acid, linear alkyl benzene sulfonic acid, xylene sulfonic acid, cumene sulfonic acid and the like. In a preferred aspect, the compositions include a strong acid having a pKa less than about 2.5 to beneficially provide the acidic use compositions having a pH less than about 4, or preferably less than about 3. In an embodiment, the compositions include a strong acid in combination with the anionic surfactant, and optionally include a weak acid.

Exemplary weak acids suitable for use modifying the pH of the compositions include alpha hydroxycarboxylic acid, such as lactic acid, citric acid, tartaric acid, malic acid, gluconic acid, and the like; carboxylic acids, such as formic acid, acetic acid, propionic acid and the like; other common organic acids such as ascorbic acid, glutamic acid, levulinic acid, etc. could also be used. In a preferred aspect, the compositions include a weak acid having a pKa greater than about 2.5 to beneficially provide the acidic use compositions having a pH less than about 4, or preferably less than about 3. In an embodiment, the compositions include a weak acid in combination with the anionic surfactant, and optionally include a strong acid. In a preferred embodiment, the composition is free of mono-carboxylic acids, di-carboxylic acids, or both mono- and di-carboxylic acids.

In a preferred embodiment, the compositions can contain less than 0.5 wt. %, preferably less than about 0.1 wt. %, more preferably less than about 0.01 wt. %, and most preferably free of a carboxylic acid, a strong acid, a weak acid, a peracid, or mixture thereof.

Solvent

In some embodiments, the compositions can comprise an organic solvent. In a preferred embodiment, the concentrated antimicrobial multi-purpose composition comprises between about 1 wt. % and about 30 wt. %, more preferably between about 2 wt. % and about 20 wt. %, and most preferably between about 5 wt. % and about 10 wt. % of a solvent. In a preferred embodiment, the ready-to-use antimicrobial multi-purpose composition comprises between about 0.01 wt. % and about 2 wt. %, more preferably between about 0.05 wt. % and about 1.5 wt. %, and most preferably between about 0.1 wt. % and about 1 wt. % of a solvent.

In a preferred embodiment, the solvent is a hydrophobic oxygenated solvent. Exemplary solvents and solvent systems include limited water-solubility alcohols. In an aspect, a benzyl alcohol solvent and/or solvent system is employed. In a further aspect, a phenoxyethanol solvent and/or solvent system is employed. Without being limited to a particular mechanism of action, in some embodiments, the solvent provides a limited water solubility alcohol providing hydrophobicity that adds affinity towards greasy soils and acts as a plasticizer. In an embodiment, the solvent has a solubility in water of preferably less than 15% water soluble, more preferably less than 8% water soluble, and most preferable less than 5% water soluble. In a preferred embodiment, the composition only contains solvent with limited water solubility. In a preferred embodiment, the compositions can comprise both a solvent with limited water solubility and also a co-solvent having slightly more water solubility.

Additional suitable solvents and solvent systems may include one or more different solvents including aromatic alcohols, ether amines, amidines, esters, glycol ethers, and mixtures thereof. Representative glycol ether solvents may include aromatic glycol ether solvents, such as ethylene glycol phenyl ether (commercially available from Dow as Dowanol Eph) or diethylene glycol phenyl ether (commercially available as Dowanol DiEPh).

Additional suitable solvents may include 1,8-Diazabicyclo[5.4.0]undec-7-ene, or also may be referred to as 2,3,4,6,7,8,9,10-Octahydropyrimidol[1,2-a]azepine (or DBU), 2.5.7.10-tetraoxaundecante (TOU), acetamidophenol, acetanilide, acetophenone, 2-acetyl-1-methylpyrrole, ethyl hexyl glycerine, benzyl acetate, benzyl alcohol, methyl benzyl alcohol, alpha phenyl ethanol, benzyl benzoate, benzyloxyethanol, ethylene glycol phenyl ether, a propylene glycol, propylene glycol phenyl ether, amyl acetate, amyl alcohol, 3-butoxyethyl-2-propanol, butyl acetate, n-butyl propionate, cyclohexanone, diacetone alcohol, diethoxyethanol, diethylene glycol methyl ether, diisobutyl carbinol, diisobutyl ketone, dimethyl heptanol, dipropylene glycol tert-butyl ether, 2-ethylhexanol, ethyl propionate, ethylene glycol methyl ether acetate, hexanol, isobutanol, isobutyl acetate, isobutyl heptyl ketone, isophorone, isopropanol, isopropyl acetate, methanol, methyl amyl alcohol, methyl n-amyl ketone, 2-methyl-1-butanol, methyl ethyl ketone, methyl isobutyl ketone, 1-pentanol, n-pentyl propionate, 1-propanol, n-propyl acetate, n-propyl propionate, propylene glycol ethyl ether, tripropylene glycol methyl ether, dipropylene glycol n-propyl ether, tripropylene glycol n-propyl ether, dipropylene glycol n-butyl ether, tripropylene glycol n-butyl ether, diethylene glycol n-butyl ether acetate, diethylene glycol monobutyl ether, ethylene glycol n-butyl ether acetate, ethylene glycol monobutyl ether, dipropylene glycol monobutyl ether, propylene glycol monobutyl ether, ethyl 3-ethoxypropionate, 2,2,4-Trimethyl-1,3-Pentanediol Monoisobutyrate, diethylene glycol monohexyl ether, ethylene glycol monohexyl ether, diethylene glycol monomethyl ether, diethylene glycol monoethyl ether, ethylene glycol methyl ether acetate, ethylene glycol monomethyl ether, dipropylene glycol monomethyl ether, propylene glycol methyl ether acetate, propylene glycol monomethyl ether, diethylene glycol monopropyl ether, ethylene glycol monopropyl ether, dipropylene glycol monopropyl ether and propylene glycol monopropyl ether. Representative dialkyl carbonates include dimethyl carbonate, diethyl carbonate, dipropyl carbonate, diisopropyl carbonate and dibutyl carbonate. Representative oils include benzaldehyde, pinenes (alphas, betas, etc.), terpineols, terpinenes, carvone, cinnamealdehyde, borneol and its esters, citrals, ionenes, jasmine oil, limonene, dipentene, linalool and its esters. Representative dibasic esters include dimethyl adipate, dimethyl succinate, dimethyl glutarate, dimethyl malonate, diethyl adipate, diethyl succinate, diethyl glutarate, dibutyl succinate, dibutyl glutarate and products available under the trade designations DBE, DBE-3, DBE-4, DBE-5, DBE-6, DBE-9, DBE-IB, and DBE-ME from DuPont Nylon. Representative phthalate esters include dibutyl phthalate, diethylhexyl phthalate and diethyl phthalate. Additional solvents include glycerin and glycerin mono alkyl ethers such as mono heptyl glycerin, and 1,2 alkane diols such as 1,2 octane diol.

In a preferred embodiment, the solvent is one or more of benzyl alcohol and/or a solvent from the Dowanol E series and/or Dowanol P series.

Methods of Cleaning

When used at an appropriate concentration, which can be indicated by the pH, the cleaning compositions provide antimicrobial efficacy when in contact with a microbial population. The compositions are also effective at removal of soils form a surface. Thus, the compositions can be used to clean a surface that is soiled and/or having a microbial population.

The methods of use for antimicrobial, including antiviral, disinfection along with inactivating viruses, include a contacting step, wherein the antimicrobial multi-purpose compositions disclosed herein are applied to a surface in need of treatment. In an embodiment, the contacting may involve contacting the antimicrobial multi-purpose composition with a food contact and/or non-food contact hard surface. Such surfaces can further include instruments, such as medical instruments. Surfaces can also include those cleaned in third-sink sanitizing, including various wares. In still further aspects, contacting the composition can be to a CIP (clean in place) application. In still further aspects, contacting the composition may be contacting the composition with a ware wash machine, such as a ware wash application. Such surfaces can include soft surfaces, ware, and/or hard surfaces. Preferred surfaces can comprise one or more of a bath, a carpet, a container, a counter, a curtain, a door, a door handle, a drain, a fabric, a floor, a fluid tank, a hospital partition, a mirror, a monitor, a pipe, a rail, a shower, a sink, a textile, a thermostat, a touch screen, an upholstery, a wall, a window, a woven surface, and a non-woven surface.

The various surfaces to which the compositions can be applied can include any conventional application means. Suitable applications can include, for example, by wiping, spraying, pouring, mopping, dipping, immersing, or the like. The contacting step allows the composition to contact the surface for a predetermined amount of time. The amount of time can be sufficient to allow, including from a few seconds to an hour, from about 30 seconds to about 15 minutes, or any range therebetween. The methods may comprise a single step of applying the composition onto the surface without direct physical removal, such as a rinse step. In an embodiment, the compositions can be on a wipe such that the wipe can be applied to a surface.

In some aspects, the methods can further include a pre-cleaning step, such as where a antimicrobial multi-purpose compositions is applied, wiped and/or rinsed, and thereafter followed by the applying of the compositions. The compositions and methods of use thereof can include treating cleaned or soiled surfaces.

All publications and patent applications in this specification are indicative of the level of ordinary skill in the art to which this invention pertains. All publications and patent applications are herein incorporated by reference to the same extent as if each individual publication or patent application was specifically and individually indicated as incorporated by reference.

EXAMPLES

It should be understood that these Examples, while indicating certain embodiments of the invention, are given by way of illustration only and are non-limiting. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

The materials used in the examples included the following:

Polystyrene resin beads functionalized with chlorine: an exemplary substrate commercially available from a variety of sources.

Sodium Chloride: an ionic salt commercially available from a variety of sources.

Sodium Carbonate: an alkalinity source commercially available from a variety of sources.

Sodium Hydroxide: an alkalinity source commercially available from a variety of sources.

Reactive Orange 16 Dye: An anionic dye belonging to the class of azo dyes.

Congo Red Dye: A benzidine-based anionic diazo dye.

m-Cresol Purple Dye: A triarylmethane dye.

Example 1

A cellulose sponge was tested with reactive dye to determine whether the reactive dye could detect changes in pH levels within a cellulose substrate. The cellulose sponge contained a highly alkaline center in comparison to a less alkaline surrounding area of the sponge. The cellulose sponge was saturated with Reactive Orange 16 dye to test its pH indicator abilities. The results are shown in FIG. 24.

Figure 24:
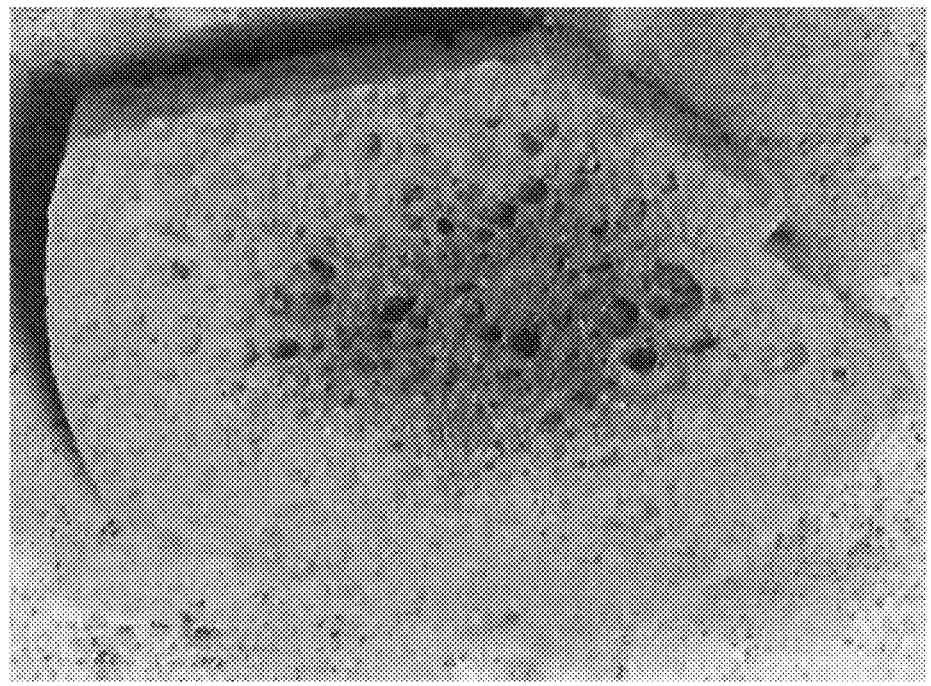
FIG. 24 is a photograph of a cellulose-based sponge that has been modified to include an pH sensitive azo-dye via a covalent bonding mechanism which shows a color change where a cleaning composition has been applied to the sponge.

As shown in FIG. 24, Reactive Orange 16 dye was successful in detecting a pH change on the cellulose sponge substrate. The area of high alkalinity resulted in a visibly darker shade than the surrounding area with a lower pH, indicating that the reactive dye was effective in providing a visual indication of pH change on a cellulose substrate.

Example 2

Reactive dyes were further tested with substrates such as functionalized porous beads to determine whether the dyes would be effective in visually detecting changes in pH. Functionalized porous beads were prepared in test tubes at various pH levels as shown in Table 1. Congo Red dye was then added to each test tube. The results are shown in FIG. 25.

TABLE 1

| Sample | pH |
|---|---|
| A | 0.05 |
| B | 0.10 |
| C | 0.23 |
| D | 0.55 |
| E | 0.9 |
| F | 1.1 |
| G | 1.3 |
| H | 2.0 |
| I | 3.0 |
| J | 7.0 |

Figure 25:
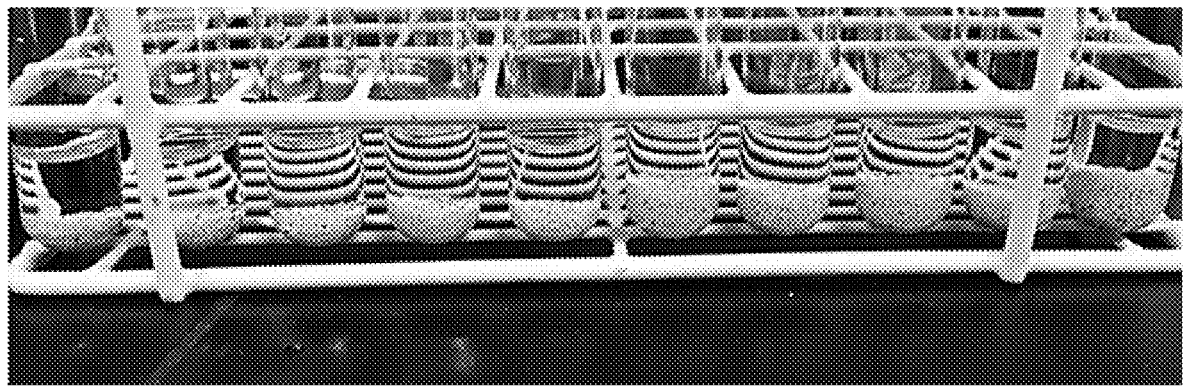
FIG. 25 is a photograph of silica beads surface functionalized and bound to an exemplary pH sensitive azo dye in liquids at differing pHs to assess the color change of the silica.

As shown in FIG. 25, Congo Red dye successfully bound to the functionalized porous beads, resulting in a gradual color change as pH increased. As the pH increased, the color of the functionalized porous beads gradually became darker in color. These results indicate that the reactive dye was effective in binding to functionalized porous beads in providing a visual change in color based on pH level.

Example 3

Reactive dyes were further evaluated for compatibility for use with paint in contemplation of coating substrate surfaces. To test compatibility with various paints, water-based and oil-based paint samples were used. Three paint samples were combined with m-Cresol Purple dye, and an additional three paint samples were combined with Reactive Orange 16. Various dyes were applied to each paint sample to determine whether the dyes would be compatible.

Figure 26:
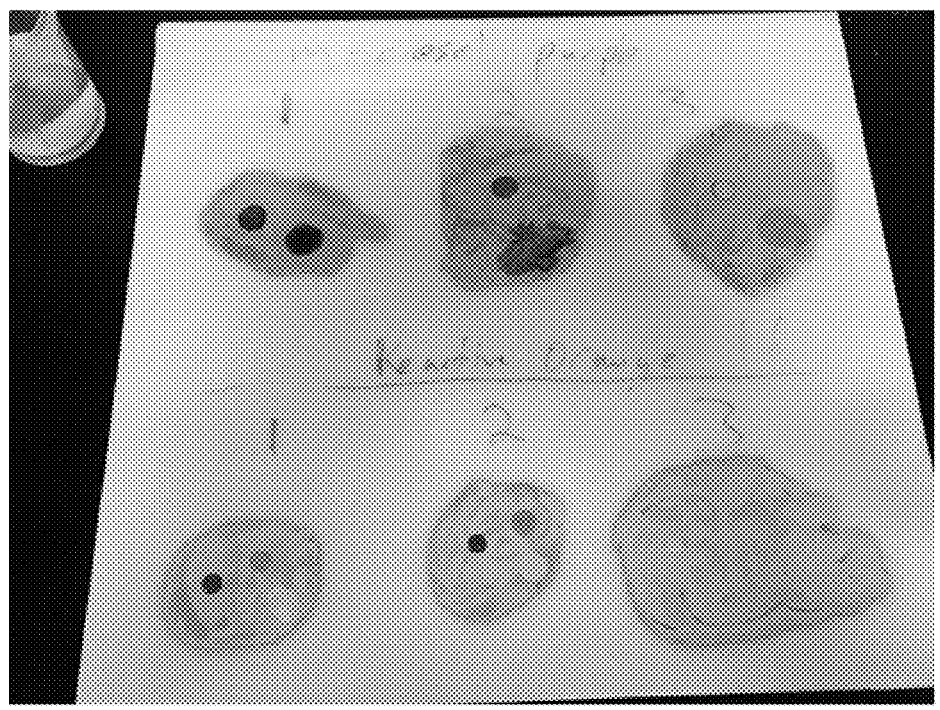
FIG. 26 is a photograph of different paint types (specifically water-based paints and oil-based paints) to assess the compatibility with pH sensitive azo dyes.

The results are shown in FIG. 26. The paint samples labeled 1 and 2 were water-based paint, whereas the paint samples labeled 3 were oil-based paint. As shown in FIG. 26, the dyes that were applied to the water-based paint resulted in distinct colors, indicating that the dyes dissolved and therefore were not compatible with water-based paint. On the other hand, the dyes that were applied to the oil-based paint did not result in a color change, indicating that the dyes did not dissolve and therefore were compatible with oil-based paint. The "colorless" drops were at pH 7 and the drops at the top and darker drops at the bottom were at pH 13.

The data in the foregoing examples demonstrates the suitability of the pH sensitive dyes, when applied to a substrate, to indicate a desired pH level (and thereby concentration) for the compositions which can be used to indicate efficacy of a cleaning composition in real-time at-a-glance.

The inventions being thus described, it will be obvious that the same may be varied in many ways. Such variations are not to be regarded as a departure from the spirit and scope of the inventions and all such modifications are intended to be included within the scope of the following claims. The above specification provides a description of the manufacture and use of the disclosed compositions and methods. No features shown or described are essential to permit basic operation of the present invention unless otherwise indicated. Since many embodiments can be made without departing from the spirit and scope of the invention, the invention resides in the claims.

The inventions being thus described, it will be obvious that the same may be varied in many ways. Such variations are not to be regarded as a departure from the spirit and scope of the inventions and all such modifications are intended to be included within the scope of the following claims. The above specification provides a description of the manufacture and use of the disclosed compositions and methods. Since many embodiments can be made without departing from the spirit and scope of the invention, the invention resides in the claims.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilized for realizing the invention in diverse forms thereof.

LIST OF REFERENCE CHARACTERS

The following reference characters and descriptors are not exhaustive, nor limiting, and include reasonable equivalents. If possible, elements identified by a reference character below and/or those elements which are near ubiquitous within the art can replace or supplement any element identified by another reference character.

100 container
102A concave lug
102B base
104 sidewall
106 upper rim
108 window
110 external pocket
112 pH strip
114 retention arms
116 upper holder
118 rivets
120 intermediate support members
122 ears
123 apertures
124 bail
126 first end of bail
128 second end of bail
130 post at first end
132 post at second end
134 product source identifier(s)
136 liquid volume indicators
138 sleeve with instructions
140 legend
142 universal hazard symbols

What is claimed is:

1. A container for determining whether an acceptable concentration of a sanitizing or disinfecting composition placed in the container is present using only an at-a-glance determination, the container comprising:
   a base including a centrally located concave lug, an upper rim, and at least one upstanding sidewall therebetween;
   a flexible retention arm at an interior of the container, attached to the at least one upstanding sidewall and/or upper rim;
   a pH sensitive indicator comprising a dye;
      wherein the pH sensitive indicator is removably secured to the container at an elevation such that an upper edge of the pH sensitive indicator lies below a lower surface of the upper rim, by way of the flexible retention arm;
      wherein the dye is an azo dye, bromothymol blue, thymol blue, m-cresol purple, phenol red, xylenol blue, xylenol orange, or a combination thereof;
      wherein the dye is bound to or coated on a cellulose-based substrate removably attached to a pail or a bucket; and
      wherein the dye exhibits a color change at a pH of about 4.5 or less; and
   at least one outer transparent surface through which the pH sensitive indicator can be observed;
   wherein the base, the upper rim, and the at least one standing sidewall are opaque and the at least one outer transparent surface comprises one or more windows, a majority of an external surface area of the container is opaque and a minority of the external surface area of the container is transparent, and an outer portion of the at least one outer transparent surface is flush with adjacent portions of the external surface of the container.

2. The container of claim 1, further comprising a bail operatively attached to the upper rim.

3. The container of claim 2, wherein the bail attaches to the upper rim through apertures located at a periphery of the upper rim.

4. The container of claim 3, wherein the apertures are located in ears positioned generally at the middle of the at least one upstanding sidewall.

5. The container of claim 1, wherein the upper rim comprises intermediate members that bridge the at least one upstanding sidewall and a lower and outward portion of the upper rim.

6. The container of claim 5, wherein the upper rim curves downwardly and outwardly so as to be gripped by a user.

7. The container of claim 1, wherein the base comprises feet.

8. The container of claim 1, wherein the at least one upstanding sidewall forms an upstanding boundary about the base and extends generally vertically upward terminating in the upper rim.

9. The container of claim 1, wherein the at least one upstanding sidewall includes sections having varying tapers relative to a vertical plane.

10. The container of claim 9, wherein an upper section of the container includes a greater outward taper relative to the vertical plane than a lower section of the container.

11. The container of claim 10, wherein the upper rim of the container has a taper relative to the vertical plane greater than the greater outward taper.

12. The container of claim 1, wherein the at least one sidewall extends generally upwardly and outwardly to flare near a mouth of the container.

13. The container of claim 1, wherein container is constructed from polypropylene.

14. The container of claim 1, wherein spare pH indicators are stored at a location adjacent the one or more windows.

15. The container of claim 1, wherein the flexible retention arms form part of a holder that is riveted to the at least one upstanding sidewall.

16. The container of claim 1, wherein the azo dye comprises one or more of a diazenyl functional group:

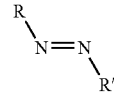

wherein R is an aryl group or an alkyl group having between 2 and 20 carbons, and wherein R' is an aryl group or an alkyl group having between 2 and 20 carbons.

17. The container of claim 1, wherein the cellulose-based substrate comprises a plastic, a metal, a textile, or cellulose-based.

18. The container of claim 17, wherein the cellulose-based substrate comprises the pail or the bucket.

19. The container of claim 18, wherein the cellulose-based substrate comprises a window.

20. The container of claim 18, wherein the at least one upstanding sidewall comprises a composite, a glass, a metal, or a combination thereof.

* * * * *